United States Patent
Son et al.

(10) Patent No.: US 10,952,694 B2
(45) Date of Patent: Mar. 23, 2021

(54) METHOD AND APPARATUS FOR CORRECTING COMPUTED TOMOGRAPHY IMAGE

(71) Applicant: HITACHI, LTD., Tokyo (JP)

(72) Inventors: Kihong Son, Suwon-si (KR); Kyoung-Yong Lee, Suwon-si (KR); Duhgoon Lee, Suwon-si (KR); Wooyoung Jang, Suwon-si (KR); Jaemoon Jo, Suwon-si (KR)

(73) Assignee: HITACHI, LTD., Tokyo (JP)

(*) Notice: Subject to any disclaimer, the term of this patent is extended or adjusted under 35 U.S.C. 154(b) by 125 days.

(21) Appl. No.: 16/285,502

(22) Filed: Feb. 26, 2019

(65) Prior Publication Data
US 2019/0261940 A1    Aug. 29, 2019

(30) Foreign Application Priority Data
Feb. 28, 2018 (KR) .................. 10-2018-0024723

(51) Int. Cl.
*A61B 6/03* (2006.01)
*A61B 6/00* (2006.01)
(Continued)

(52) U.S. Cl.
CPC ............ *A61B 6/5264* (2013.01); *A61B 6/032* (2013.01); *A61B 6/4452* (2013.01); *A61B 6/461* (2013.01);
(Continued)

(58) Field of Classification Search
CPC ..... A61B 6/5264; A61B 6/463; A61B 6/4452; A61B 6/461; A61B 6/032; G06T 11/008;
(Continued)

(56) References Cited

U.S. PATENT DOCUMENTS 9,710,936 B2   7/2017 Schretter et al.
10,032,295 B2  7/2018 Lee et al.
(Continued)

FOREIGN PATENT DOCUMENTS

JP   2014-194635 A   10/2014
JP   10-1480036      1/2015
(Continued)

OTHER PUBLICATIONS

International Search Report and the Written Opinion of the International Searching Authority dated Jun. 3, 2019 from International Patent Application No. PCT/KR2019/002129, 11 pages.

*Primary Examiner* — Chuong A Ngo
(74) *Attorney, Agent, or Firm* — Cooper & Dunham LLP

(57) ABSTRACT

A method and apparatus correct a computed tomography (CT) image with motion artifacts. The method of correcting a CT image may include: obtaining a reconstruction image of an object by reconstructing an X-ray projection image; measuring a parameter value related to motion artifacts that occur due to movement of the object in at least one of the X-ray projection image or the reconstruction image; calculating a correction possibility for the reconstruction image based on the measured parameter value; and determining whether to perform correction on the reconstruction image based on the calculated correction possibility.

17 Claims, 19 Drawing Sheets

(51) Int. Cl.
*G06T 11/00* (2006.01)
*G06T 7/246* (2017.01)

(52) U.S. Cl.
CPC .............. *A61B 6/463* (2013.01); *G06T 7/246* (2017.01); *G06T 11/008* (2013.01); *G06T 2207/10081* (2013.01); *G06T 2207/20081* (2013.01); *G06T 2211/412* (2013.01)

(58) Field of Classification Search
CPC ........... G06T 7/246; G06T 2207/20081; G06T 2211/412; G06T 2207/10081; G06T 2207/20076; G06T 2207/20084; G06T 2207/20104
See application file for complete search history.

(56) References Cited

U.S. PATENT DOCUMENTS

| | | | |
|---|---|---|---|
| 10,083,526 | B2 | 9/2018 | Hagiwara |
| 2003/0083565 | A1 | 5/2003 | Toth et al. |
| 2014/0270450 | A1 | 9/2014 | Grass et al. |
| 2016/0135774 | A1* | 5/2016 | Ono ..................... A61B 6/4241 378/5 |
| 2016/0180525 | A1* | 6/2016 | Reynolds .............. G06T 7/0016 382/131 |
| 2016/0300370 | A1 | 10/2016 | Yoo et al. |
| 2016/0310082 | A1 | 10/2016 | Rajamani et al. |
| 2017/0242088 | A1 | 8/2017 | Oh et al. |

FOREIGN PATENT DOCUMENTS

| | | |
|---|---|---|
| JP | 2017-60566 | 3/2017 |
| JP | 10-1775556 | 8/2017 |
| WO | 2014/036473 A1 | 3/2014 |

* cited by examiner

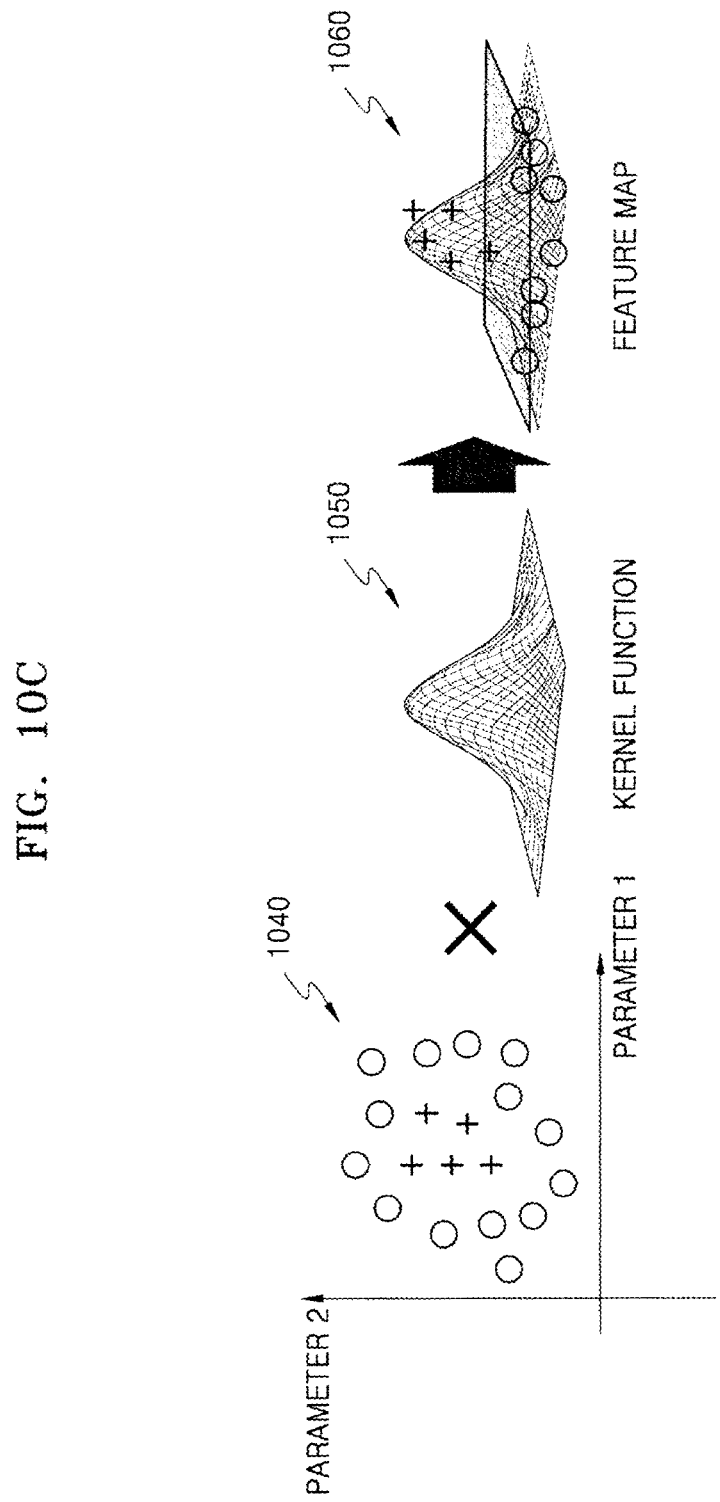

METHOD AND APPARATUS FOR CORRECTING COMPUTED TOMOGRAPHY IMAGE

CROSS-REFERENCE TO RELATED APPLICATION(S)

This application is based on and claims priority under 35 U.S.C. § 119 to Korean Patent Application No. 10-2018-0024723, filed on Feb. 28, 2018, in the Korean Intellectual Property Office, the disclosure of which is incorporated by reference herein in its entirety.

BACKGROUND

1. Field

The disclosure relates to methods and apparatuses for removing motion artifacts induced due to movement of an object during computed tomography (CT) imaging and correcting a CT image.

2. Description of Related Art

Medical imaging apparatuses are used to obtain images showing an internal structure of an object. The medical imaging apparatuses are non-invasive examination apparatuses that capture and process images of details of structures, tissue, fluid flow, etc., inside a body and display the images to a user. A user, e.g., a medical practitioner, may use medical images output from the medical imaging apparatuses to diagnose a patient's condition and diseases.

A computed tomography (CT) apparatus is a representative example of an apparatus for imaging an object by emitting X-rays toward a patient. A CT apparatus is capable of providing a cross-sectional image of an object and may represent an internal structure (e.g., organs such as a kidney, a lung, etc.) of the object without superimposition of adjacent structures, as compared to a general X-ray apparatus. Due to these advantages, CT apparatuses have been widely used for precise diagnosis of diseases.

When a patient to be imaged, i.e., an object, moves during CT imaging, blur may occur in a CT image. Such blurring may degrade the sharpness of the CT image to make image analysis difficult. Image distortion, blurring, degradation of image sharpness, etc., occurring in a CT image due to patient movement are collectively referred to as motion artifacts. To remove the motion artifacts, image correction needs to be performed.

According to the related art, a technique for correcting a CT image involves identifying a region of interest (ROI) in a CT image, measuring a signal used as the basis for estimating a patient's motion via a sensor such as an electrocardiogram (ECG) sensor, a probe, a positional sensor, or the like, and estimating the extent of the patient's motion for correction based on characteristics of the measured signal. However, in the technique of the related art, because the extent of the patient's motion has to be estimated before correction, it may be difficult to specify a region requiring correction in the CT image, and the accuracy of correction may be low. Another drawback is that unnecessary operations such as specifying an ROI may degrade efficiency.

SUMMARY

Provided are methods and apparatuses for correcting a computed tomography (CT) image, and in particular, correction methods and apparatuses for measuring a value of a parameter related to motion artifacts in an X-ray projection image of an object and a reconstruction image obtained by reconstructing a plurality of X-ray projection images and calculating a correction possibility for a CT image based on the measured value.

Additional aspects will be set forth in part in the description which follows and, in part, will be apparent from the description, or may be learned by practice of the presented embodiments of the disclosure According to an embodiment of the disclosure, a method of correcting a CT image includes: obtaining a reconstruction image of an object by reconstructing an X-ray projection image; measuring a parameter value related to motion artifacts that occur due to movement of the object in at least one of the X-ray projection image or the reconstruction image; calculating a correction possibility for the reconstruction image based on the measured parameter value; and determining whether to perform correction on the reconstruction image based on the calculated correction possibility.

The calculating of the correction possibility may include: measuring at least one of a sharpness value or an entropy value in the reconstruction image; and removing motion artifacts in the reconstruction image based on the measured at least one of the sharpness value or the entropy value and calculating a probability of correcting the reconstruction image.

The parameter may include at least one of a sharpness value or an entropy value of the reconstruction image. The method may further include setting a region to be corrected by recognizing a position of the motion artifacts occurring in the reconstruction image based on the measured parameter value. The calculating of the correction possibility may include calculating a correction possibility for the set region to be corrected based on a parameter value measured in the set region.

The method may further include receiving a user input of setting a region to be corrected in the reconstruction image, and the calculating of the correction possibility may include calculating a correction possibility for the region to be corrected, which is set according to the received user input, based on a parameter value measured in the set region.

The measuring of the parameter value may include measuring a relative change in positions of edges in a plurality of X-ray projection images acquired by emitting X-rays toward the object at different time points.

The measuring of the parameter value may include: measuring a first position that is a position of an edge in a first X-ray projection image acquired at a first angular position; and measuring a second position that is a position of an edge in a second X-ray projection image acquired at the first angular position after moving the object by a pitch having a preset interval in a first direction. The calculating of the correction possibility may include calculating the correction possibility by quantifying a difference between the pitch and a difference between the first and second positions.

The method may further include: storing a correction result value with respect to the parameter value, which is received from a user; and training a correlation between the received correction result value and the parameter value by using machine learning. The calculating of the correction possibility may include updating an equation used to calculate the correction possibility by receiving the trained correlation as feedback data.

The method may further include displaying the calculated correction possibility.

The displaying of the correction possibility may include displaying a color mapping image obtained by mapping a color corresponding to a calculated correction probability value onto the reconstruction image.

The method may further include displaying a user interface (UI) indicating an expected time needed to perform the correction when it is determined that the correction is to be performed on the reconstruction image.

The method may further include displaying a corrected image obtained by performing the correction with respect to the reconstruction image in a first region and the reconstruction image on which the correction has not been performed in a second region.

According to another embodiment of the disclosure, a CT apparatus includes: an X-ray source configured to emit X-rays toward an object at a plurality of angular positions arranged around the object; an X-ray detector configured to detect the X-rays that have passed through the object at positions corresponding to the plurality of angular positions; a data acquisitor configured to acquire a plurality of X-ray projection images by using the X-rays detected by the X-ray detector; an image generator configured to generate a reconstruction image by reconstructing the plurality of X-ray projection images; and a processor configured to measure a parameter value related to motion artifacts that occur due to movement of the object in at least one of each of the plurality of X-ray projection images or the reconstruction image, calculate a correction possibility for the reconstruction image based on the measured parameter value, and determine whether to perform correction on the reconstruction image based on the calculated correction possibility.

The processor may be further configured to measure at least one of a sharpness value or an entropy value in the reconstruction image, remove motion artifacts in the reconstruction image based on the measured at least one of the sharpness value or the entropy value, and calculate a probability of correcting the reconstruction image.

The parameter value may include at least one of a sharpness value or an entropy value of the reconstruction image, and the processor may be further configured to set a region to be corrected by recognizing a position of the motion artifacts occurring in the reconstruction image based on the measured parameter value and calculate a correction possibility for the set region to be corrected based on a parameter value measured in the set region.

The CT apparatus may further include a user inputter configured to receive a user input of setting a region to be corrected in the reconstruction image, and the processor may be further configured to set the region to be corrected based on the received user input and calculate a correction possibility for the region to be corrected based on a parameter value measured in the region to be corrected.

The processor may be further configured to measure a first position that is a position of an edge in a first X-ray projection image acquired at a first angular position, measure a second position that is a position of an edge in a second X-ray projection image acquired at the first angular position after moving the object by a pitch having a preset interval in a first direction, and calculate the correction possibility by quantifying a difference between the pitch and a difference between the first and second positions.

The processor may include: a memory storing a correction result value with respect to the parameter value, which is received from a user; and a machine learning module configured to train a correlation between the received correction result value and the parameter value by using machine learning and update an equation used to calculate the correction possibility by receiving the trained correlation as feedback data.

The CT apparatus may further include a display displaying the calculated correction possibility.

The display may display a color mapping image obtained by mapping a color corresponding to a calculated correction probability value onto the reconstruction image.

The display may display a corrected image obtained by performing the correction with respect to the reconstruction image in a first region and the reconstruction image on which the correction has not been performed in a second region.

According to another embodiment of the disclosure, a computer program product includes a computer-readable storage medium including instructions for: obtaining a reconstruction image of an object by reconstructing an X-ray projection image; measuring a parameter value related to motion artifacts that occur due to movement of the object in at least one of the X-ray projection image or the reconstruction image; calculating a correction possibility for the reconstruction image based on the measured parameter value; and determining whether to perform correction on the reconstruction image based on the calculated correction possibility.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 10C is a graph which illustrates a method, performed by a machine learning module, of training a correlation between a parameter related to motion artifacts in a CT image and a correction result value received from a user by using an SVM algorithm, according to an embodiment of the disclosure;

DETAILED DESCRIPTION

Figure 1:
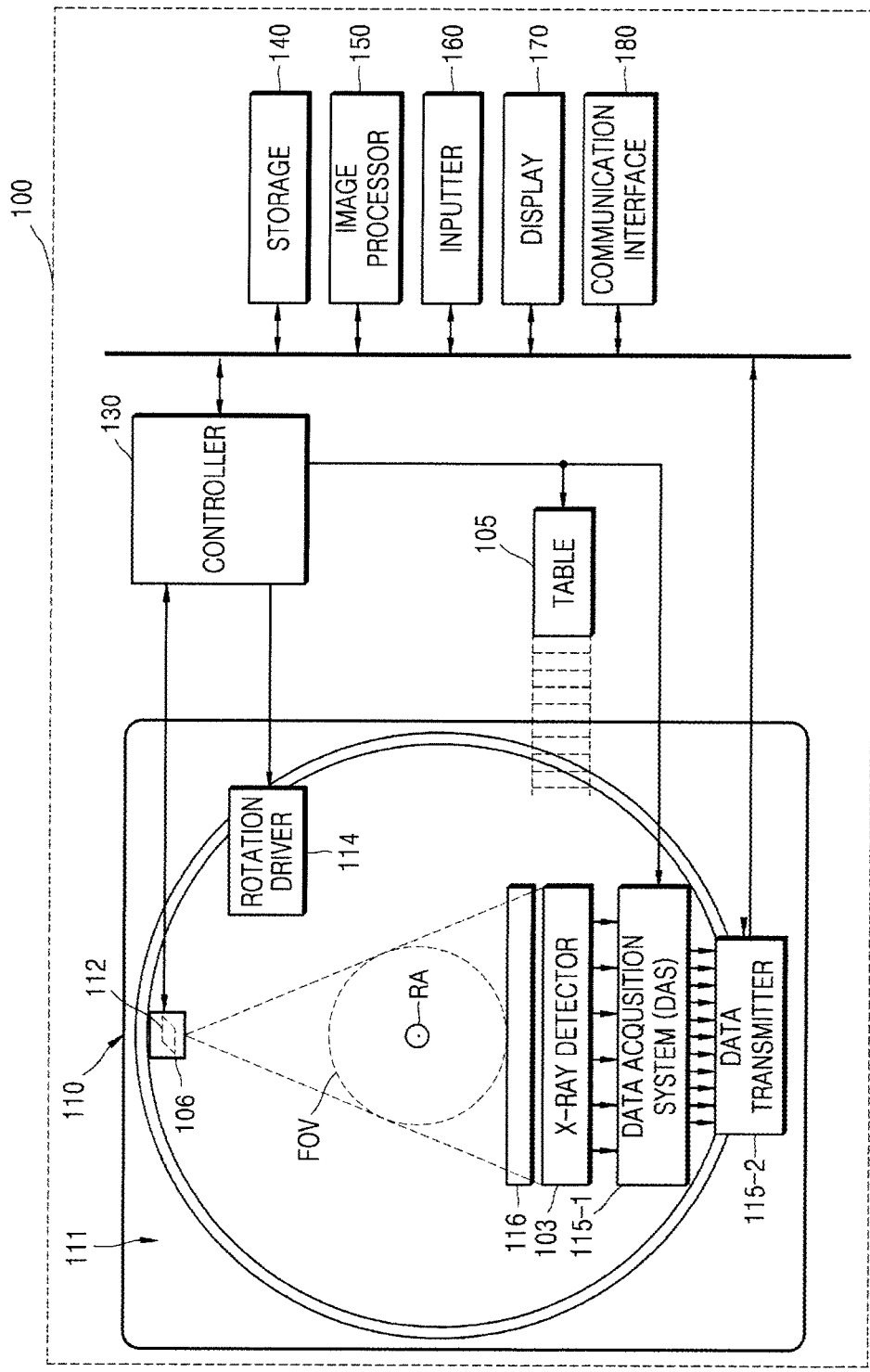
FIG. 1 is a diagram of a computed tomography (CT) system according to an embodiment of the disclosure.

The principle of the disclosure is explained and embodiments are disclosed so that the scope of the disclosure is clarified and one of ordinary skill in the art to which the disclosure pertains implements the disclosure. The disclosed embodiments may have various forms.

Throughout the specification, like reference numerals or characters refer to like elements. In the present specification, all elements of embodiments are not explained, but general matters in the technical field of the disclosure or redundant matters between embodiments of the disclosure will not be described. Terms 'part' and 'portion' used herein may be implemented using software or hardware, and, According to embodiments of the disclosure, a plurality of 'parts' or 'portions' may be implemented using a single unit or element, or a single 'part' or 'portion' may be implemented using a plurality of units or elements. The operational principle of the disclosure and embodiments thereof will now be described more fully with reference to the accompanying drawings.

In the present specification, an image may include a medical image obtained by a medical imaging apparatus, such as a computed tomography (CT) apparatus, a magnetic resonance imaging (MRI) apparatus, an ultrasound imaging apparatus, or an X-ray apparatus.

Throughout the specification, the term 'object' is a thing to be imaged, and may include a human, an animal, or a part of a human or animal. For example, the object may include a part of a body (i.e., an organ), a phantom, or the like.

In the present specification, a 'CT system' or 'CT apparatus' refers to a system or apparatus configured to emit X-rays while rotating around at least one axis relative to an object and photograph the object by detecting the X-rays.

In the specification, a 'CT image' refers to an image constructed from raw data obtained by photographing an object by detecting X-rays that are emitted as the CT system or apparatus rotates about at least one axis with respect to the object.

Throughout the disclosure, the expression "at least one of a, b or c" indicates only a, only b, only c, both a and b, both a and c, both b and c, all of a, b, and c, or variations thereof.

FIG. 1 illustrates a structure of a CT system 100 according to an embodiment of the disclosure.

The CT system 100 may include a gantry 110, a table 105, a controller 130, a storage 140, an image processor 150, an inputter 160, a display 170, and a communication interface 180.

The gantry 110 may include a rotating frame 111, an X-ray generator 112, an X-ray detector 103, a rotation driver 114, and a readout device 115. The gantry 110 may further include a stator and a rotor rotating together with a component such as the X-ray generator 112.

The rotor may include the rotating frame 111 having an annular shape with a rotation axis (RA) at the center. The rotating frame 111 may include a slip ring (not shown). The rotating frame 111 may also receive a driving signal from the rotation driver 114 in order to rotate. The rotating frame 111 may receive the driving signal and power from the rotation driver 114 while contacting the rotation driver 114 via the slip ring. A motor may provide a driving force to the rotating frame 111, and a bearing (not shown) may support the rotating frame 111.

X-ray radiation that reaches the X-ray detector 103 includes attenuated primary radiation that forms an image and scattered radiation that deteriorates the quality of an image. An anti-scatter grid 116 may be disposed between an object and the X-ray detector 103 and may transmit most of primary radiation and attenuate scattered radiation. The object may be positioned on the table 105 which may move, tilt, or rotate during a CT scan.

The X-ray generator 112 receives a voltage and a current from a high voltage generator (HVG) to generate and emit X-rays. The X-rays emitted by the X-ray generator 112 may be shaped as a cone beam or parallel beam.

The CT system 100 may be implemented as a single-source CT system including one X-ray generator 112 and one X-ray detector 103, or as a dual-source CT system including two X-ray generators 112 and two X-ray detectors 103.

The X-ray detector 103 detects radiation that has passed through the object. For example, the X-ray detector 103 may detect radiation by using a scintillator, a photon counting detector, etc.

Methods of driving the X-ray generator 112 and the X-ray detector 103 may vary depending on scan modes used for scanning of the object. The scan modes are classified into an axial scan mode and a helical scan mode, according to a path along which the X-ray detector 103 moves. Furthermore, the scan modes are classified into a prospective mode and a retrospective mode, according to a time interval during which X-rays are emitted.

The controller 130 may control an operation of each of the components of the CT system 100. The controller 130 may include a memory configured to store program for performing a function or data and a processor configured to process the program codes or the data. The controller 130 may be implemented in various combinations of at least one memory and at least one processor. The processor may generate or delete a program module according to an operating status of the CT system 100 and process operations of the program module.

The readout device 115 receives a detection signal generated by the X-ray detector 103 and outputs the detection signal to the image processor 150. The readout device 115 may include a data acquisition system (DAS) 115-1 and a data transmitter 115-2. The DAS 115-1 uses at least one amplifying circuit to amplify a signal output from the X-ray detector 103, and outputs the amplified signal. The data transmitter 115-2 uses a circuit such as a multiplexer (MUX) to output the signal amplified in the DAS 115-1 to the image processor 150. According to a slice thickness or a number of slices, only some of a plurality of pieces of data collected by the X-ray detector 103 may be provided to the image processor 150, or the image processor 150 may select only some of the plurality of pieces of data.

The image processor 150 obtains tomography data from a signal obtained by the readout device 115 (e.g., pure data that is data before being processed). The image processor 150 may pre-process the obtained signal, convert the obtained signal into tomography data, and post-process the tomography data. The image processor 150 may perform some or all of the processes described herein, and the type or order of processes performed by the image processor 150 may vary according to embodiments.

According to embodiments of the disclosure, the image processor 150 may perform some or all of the processes for reconstructing a tomography image, to thereby generate the tomography data. According to an embodiment of the disclosure, the tomography data may be in the form of data that has filtered back-projection, or in the form of a tomography image. According to embodiments of the disclosure, additional processing may be performed on the tomography data by an external device such as a server, a medical apparatus, or a portable device.

Raw data is a set of data values corresponding to intensities of X-rays that have passed through the object, and may include projection data or a sinogram. The data that has undergone back-projection is obtained by performing back-projection on the raw data by using information about an angle at which X-rays are emitted. The tomography image is obtained by using image reconstruction techniques including back-projection of the raw data.

The storage 140 is a storage medium for storing control-related data, image data, etc., and may include a volatile or non-volatile storage medium.

The inputter 160 receives control signals, data, etc., from a user. For example, the control signals may include a control signal for controlling an imaging operation, a control signal for controlling display of a medical image, etc.

The display 170 may display information indicating an operational status of the CT system 100, medical information, medical image data, etc.

The CT system 100 includes the communication interface 180 and may be connected to external devices, such as a server, a medical apparatus, and a portable device (smartphone, tablet personal computer (PC), wearable device, etc.), via the communication interface 180.

The communication interface 180 may include one or more components that enable communication with an external device. For example, the communication interface 180 may include a short distance communication module, a wired communication module, and a wireless communication module.

The communication interface 180 may receive control signals and data from an external device and transmit the received control signals to the controller 130 so that the controller 130 may control the CT system 100 according to the received control signals.

Alternatively, by transmitting a control signal to an external device via the communication interface 180, the controller 130 may control the external device according to the control signal.

For example, the external device may process its own data according to a control signal received from the controller 130 via the communication interface 180.

A program for controlling the CT system 100 may be installed on the external device and may include instructions for performing some or all of the operations of the controller 130.

The program may be preinstalled on the external device, or a user of the external device may download the program from a server that provides an application for installation. The server that provides an application may include a recording medium having the program recorded thereon.

According to embodiments of the disclosure, the CT system 100 may or may not use a contrast medium during CT imaging, or may be implemented as an apparatus associated with another apparatus.

Figure 2:
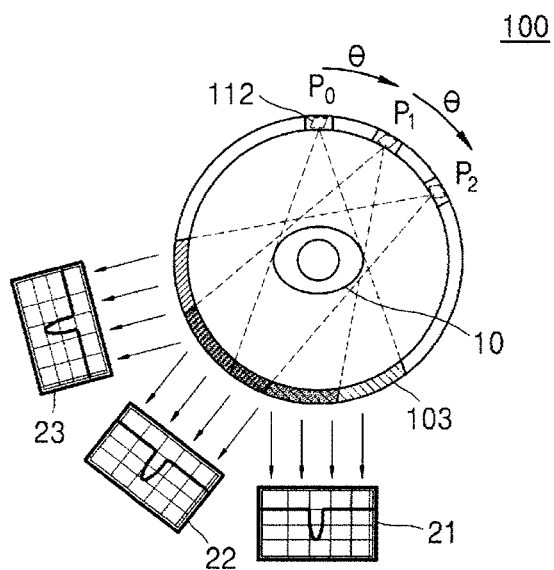
FIG. 2 is a diagram illustrating an operation of a CT system acquiring an X-ray projection image and a reconstruction image, according to an embodiment of the disclosure.
Figure 2:
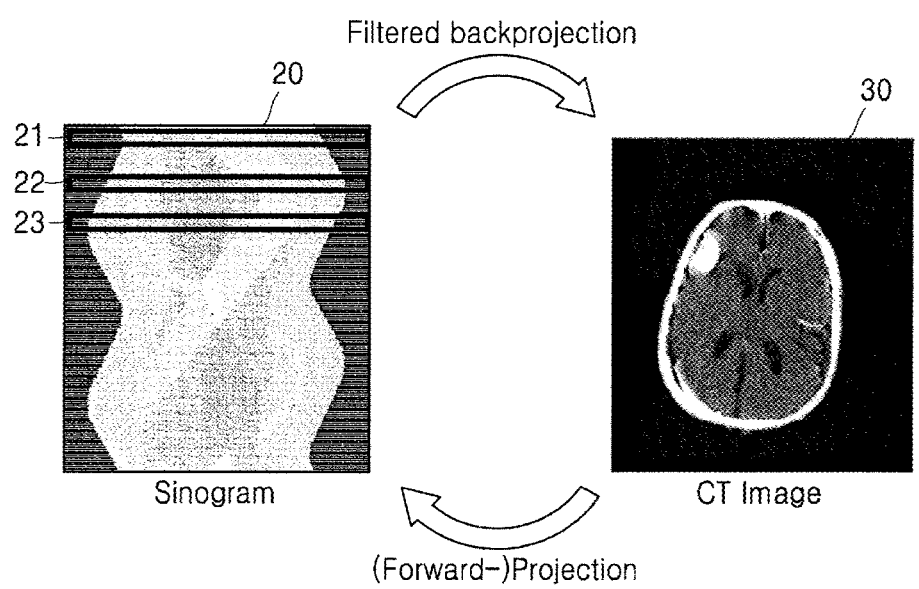

FIG. 2 illustrates an operation of a CT system 100 acquiring a plurality of pieces of X-ray projection data 21, 22, and 23 and a CT image 30, according to an embodiment of the disclosure.

Referring to FIG. 2, the CT system 100 may be an apparatus for reconstructing an image from data acquired using X-rays that have passed through an object 10, but is not limited thereto. The CT system 100 may be implemented as an optical coherence tomography (OCT) device or a positron emission tomography (PET)-CT device. A cross-sectional image obtained using the CT system 100 of FIG. 2 is referred to as a CT image 30. The CT image 30 is reconstructed from X-ray projection images by using a method such as back-projection, and may be defined as a reconstruction image.

To obtain the CT image 30, CT imaging is performed on the object 10 by using the CT system 100 to acquire raw data. The acquired raw data is then used to reconstruct the CT image 30. In this case, the raw data may be projection data acquired by projecting X-rays onto the object 10, or may be a sinogram 20 representing a set of projection data.

For example, to obtain the CT image 30, image reconstruction may be performed using the sinogram 20 acquired by performing the CT imaging.

In detail, the CT system 100 generates and emits an X-ray towards the object 10 via the X-ray generator 112 and detects the X-ray that has passed through the object 10 by using the X-ray detector 103. The X-ray detector 103 may also generate raw data corresponding to the detected X-ray.

According to an embodiment of the disclosure, while rotating along a rotating frame with the object 10 at its center, the X-ray generator 112 included in the CT system 100 may emit X-rays towards the object 10 at a position corresponding to an angle by which the X-ray generator 112 rotates. The X-ray detector 103 may detect the X-rays that have passed through the object 10 at a position opposite to the X-ray generator 112. In the embodiment shown in FIG. 2, the X-ray generator 112 emits X-rays toward the object 10 at a zero-th angular position P0 and then at a first angular position P1 after rotating by a preset angle θ. Similarly, the X-ray generator 112 may emit X-rays toward the object 10 at a second angular position P2 after rotating from the first angular position P1 by the preset angle θ.

The X-ray detector 103 may detect the X-rays that have passed through the object 10 at positions respectively arranged opposite the X-ray generator 112 at the zero-th, first, and second angular positions P0, P1, and P2. The CT system 100 may amplify signals corresponding to the detected X-rays to acquire raw data that may be the pieces of X-ray projection data 21, 22, and 23. The pieces of X-ray projection data 21, 22, and 23 acquired as the X-ray generator 112 moves at predetermined angle (e) intervals may be combined to acquire the sinogram 20. The sinogram 20 is acquired by performing CT imaging as the X-ray generator 112 rotates for one period. The sinogram 20 corresponding to one-period rotation may be used to produce a cross-sectional CT image. The one-period rotation may be rotation by an angle that may be greater than or equal to 180 degrees or by an angle that may be greater than or equal to 360 degrees depending on specifications for the CT system 100.

The CT image 30 may be reconstructed by performing filtered back-projection (FBP) on the sinogram 20.

In general, it takes about 0.2 seconds for the X-ray generator 112 to rotate 180 degrees. When the object 10 to be imaged, i.e., the patient, moves during CT imaging, blur may occur in the CT image 30 due to motion of the object 10. Such blurring may degrade the sharpness of the CT image 30 to make image analysis difficult. Blurring, degradation of image sharpness, image distortion, etc. occurring in the CT image 30 due to motion of the object 10 are referred to as motion artifacts.

In detail, when the object 10 moves, an unexpected change may occur with respect to at least one of a shape, a size, or a position of the object 10. In other words, the pieces of X-ray projection data 21, 22, and 23 acquired as the X-ray generator 112 emits X-rays toward the object 10 during one-period rotation may be pieces of X-ray projection data corresponding to different shapes of the object 10. Thus, when the CT image 30 is reconstructed by performing back-projection on the acquired pieces of X-ray projection data 21, 22, and 23, motion artifacts may occur in the CT image 30.

According to embodiments of the disclosure, there are provided a method and apparatus for measuring a parameter value related to motion artifacts in the CT image 30 and the pieces of X-ray projection data 21, 22, and 23 with respect to the object 10 and calculating a correction possibility for the CT image 30 based on the measured parameter value, as described in more detail below.

Figure 3:
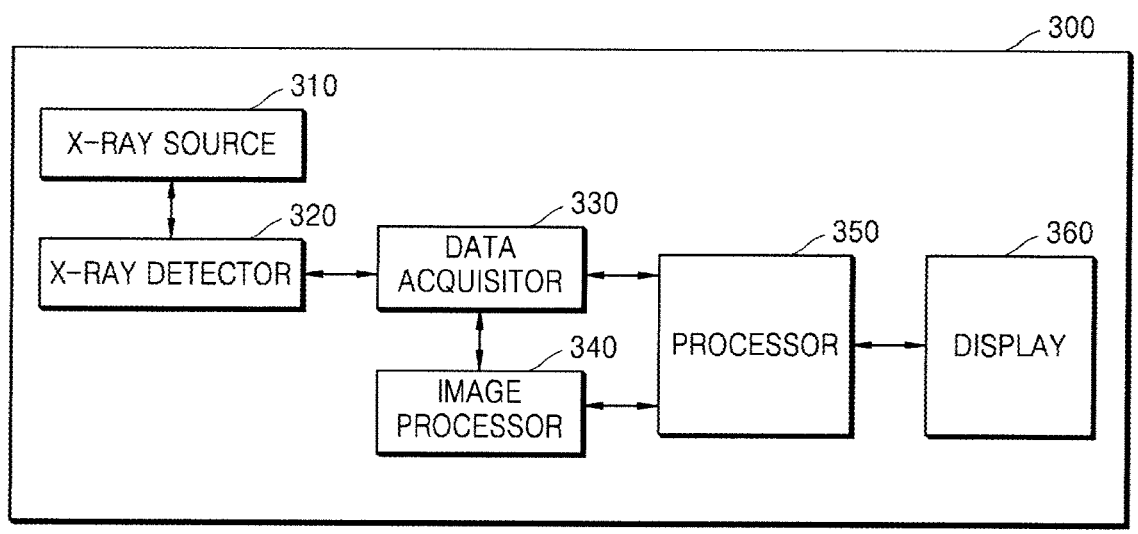
FIG. 3 is a block diagram illustrating components of a CT apparatus according to an embodiment of the disclosure.

FIG. 3 is a block diagram illustrating components of a CT apparatus 300 according to an embodiment of the disclosure.

Referring to FIG. 3, the CT apparatus 300 may include an X-ray source 310, an X-ray detector 320, a data acquisitor 330, an image processor 340, a processor 350, and a display 360. Because FIG. 3 illustrates only essential components of the CT apparatus 300, the CT apparatus 300 may further include a gantry, a rotating frame, a table, and a communication unit. According to an embodiment of the disclosure, the CT apparatus 300 may further include a user inputter configured to receive a user input of setting a region to be corrected in a reconstruction image.

The X-ray source 310 may generate X-rays and emit the generated X-rays toward an object (e.g., a patient) while moving on a rotating frame positioned around the object. According to an embodiment of the disclosure, the X-ray source 310 may emit X-rays toward the object at a plurality of angular positions (e.g., P0, P1, and P2 in FIG. 2) while rotating on the rotating frame at preset angle (e) intervals. For example, the X-ray source 310 may emit X-rays toward the object while rotating at one (1)-degree intervals. In this case, the X-ray source 310 may emit X-rays toward the object at angular positions corresponding to 1°, 2°, 3°, . . . .

The X-ray detector 320 may detect the X-rays emitted by the X-ray source 210 toward the object. The X-ray detector 320 may detect X-rays emitted at a plurality of angles by which the X-ray source 310 rotates. For example, when the X-ray source 310 emits X-rays toward the object at angular positions of 1°, 2°, 3°, . . . , the X-ray detector 320 may detect the X-rays emitted at the angular positions of 1°, 2°, 3°, . . . .

The data acquisitor 330 may acquire raw data output from the X-ray detector 320. The raw data may include a plurality of pieces of X-ray projection data. The data acquisitor 330 may include at least one amplifying circuit that may be used to amplify the pieces of X-ray projection data. The data acquisitor 330 of FIG. 3 may correspond to the DAS 115-1 described with reference to FIG. 1. According to an embodiment of the disclosure, the data acquisitor 330 may acquire a plurality of X-ray projection images from the X-ray detector 320 that detects X-rays emitted by the X-ray source 310 at the angular positions as the X-ray source 310 rotates about an axis disposed at a center of the object at preset angle intervals. According to an embodiment of the disclosure, the data acquisitor 330 may form a sinogram by sequentially stacking the X-ray projection images respectively corresponding to the angular positions.

The image processor 340 may generate a reconstruction image by reconstructing the X-ray projection images. The image processor 340 may pre-process a signal received from the data acquisitor 330, convert the received signal into tomography data, and post-process the tomography data. The image processor 340 may perform some or all of the processes for reconstructing a CT image, to thereby generate the tomography data. According to an embodiment of the disclosure, the image processor 340 may generate a CT image by performing back-projection on the pieces of X-ray projection data based on information about angular positions at which the X-ray source 310 emits X-rays.

The image processor 340 may reconstruct a CT image from the X-ray projection images by using various reconstruction methods. For example, the image processor 340 may reconstruct a CT image by using filtered back projection (FBP), an iterative method, etc.

Back-projection is a technique for reconstructing an image by adding up projection data acquired at a plurality of angular positions back across an image plane. In detail, the back-projection method allows acquisition of an image similar to a real image by using X-ray projection images acquired at the plurality of angular positions. Furthermore, filtering may be performed additionally to remove artifacts present in a reconstruction image and improve quality of the reconstruction image.

FBP is a method that improves the performance of back-projection in order to remove artifacts or blurring that may occur during the back-projection. In the FBP method, raw data is filtered prior to back-projection and then back-projected to reconstruct a CT image. The FBP method is the most commonly used in CT image reconstruction, is easy to implement, and is effective in terms of the amount of computations required for image reconstruction.

The processor 350 may measure a parameter value related to motion artifacts that occur due to motion of an object in at least one of an X-ray projection image or a CT image reconstructed from the X-ray projection image (hereinafter referred to as a 'reconstruction image'), calculate a correction possibility for the reconstruction image based on the measured parameter value, and determine whether to perform correction on the reconstruction image by using the calculated correction possibility. When calculating the correction possibility, the processor 350 may predict a CT image to be captured in an environment where there is no movement of the object based on motion artifacts in the reconstruction image. A correction possibility means a possibility of correcting the reconstruction image to coincide with the predicted CT image, i.e., a correction probability value.

The processor 350 may be formed as a hardware unit having computational capabilities of measuring a parameter value related to motion artifacts and calculating a correction possibility for a reconstruction image based on the measured parameter value. For example, the processor 350 may be constituted by at least one of a central processing unit (CPU), a microprocessor, or a graphics processing unit.

A parameter value related to motion artifacts may include at least one of a sharpness value or an entropy value measured in a reconstruction image. The processor 350 may measure a sharpness value and an entropy value in a CT image reconstructed from X-ray projection images. Image sharpness is a parameter representing the degree of image clarity, and an image having a higher sharpness value becomes clearer, and accordingly, a correction possibility for the image becomes higher. According to an embodiment of the disclosure, the processor 350 may measure a sharpness value in a reconstructed CT image by using at least one of total variation, $L_2$-norm for gradient, negative variance, or gradient variance, but embodiments of the disclosure are not limited thereto. The processor 350 may measure the degree of blur in a reconstruction image by using techniques known in the field of image processing and measure sharpness of the reconstruction image for quantification.

Furthermore, the processor 350 may measure an entropy value in a reconstructed CT image by using Equation (1) below:

$$H(\Phi) = -\sum_{h} p(h; \Phi)\log p(h; \Phi) \quad (1)$$

where $\Phi$ is a parameter value on each axis of a pixel in a reconstructed CT image and p is a probability value for each pixel.

An entropy value calculated using Equation (1) means a degree of freedom or degree of disorder of pixel values in a reconstructed CT image and is inversely proportional to a correction possibility for the reconstructed CT image. In other words, when an entropy value decreases, a correction possibility increases.

The processor 350 may recognize, based on at least one of a sharpness value or an entropy value measured in a reconstructed CT image, a position and an intensity of motion artifacts occurring in a CT image or a region therein. In an embodiment of the disclosure, when a measured parameter value, i.e., at least one of measured sharpness or entropy value, is greater or less than a preset threshold, the processor 350 may determine that motion artifacts are present in the CT image or the region. For example, when the measured sharpness value is less than a threshold preset with respect to image sharpness, the processor 350 may determine that motion artifacts are present in the CT image or the region. Furthermore, when the measured entropy value is greater than a threshold preset with respect to entropy, the processor 350 may determine that motion artifacts are present in the CT image or the region.

According to an embodiment of the disclosure, the processor 350 may recognize a position and an intensity of motion artifacts occurring in a reconstruction image, based on at least one of a mean sharpness value, a maximum sharpness value, a mean entropy value, or a maximum entropy value.

The processor 350 may quantify a correction possibility for a reconstructed CT image based on a preset equation for a measured parameter. According to an embodiment of the disclosure, the processor 350 may calculate a correction possibility for a reconstruction image as a probability value by using at least one of a sharpness value or an entropy value measured in the reconstructed CT image. An equation for calculating a correction possibility by using a sharpness value and an entropy value may be stored in a memory or a server.

According to an embodiment of the disclosure, the processor 350 may compare a sharpness value measured in a reconstructed CT image with a threshold preset with respect to image sharpness to thereby quantify a difference between the measured sharpness value and the preset threshold and calculate a correction possibility for the reconstructed CT image as a probability value based on the quantified difference. For example, the processor 350 may quantify how large or small an entropy value measured in a reconstructed CT image is compared with a threshold set with respect to entropy and calculate a probability of correction based on a quantified result.

The processor 350 may calculate a correction possibility based on parameters measured in a reconstructed CT image as well as in an X-ray projection image. According to an embodiment of the disclosure, the processor 350 may acquire pieces of position information of an object in a plurality of X-ray projection images from the same angular position at different time points and calculate a correction possibility based on the acquired pieces of position information. In detail, the processor 350 may respectively measure positions of the object in an X-ray projection image acquired by emitting X-rays from a specific angular position at a certain time point and in an X-ray projection image acquired by emitting X-rays from a position to which the object is moved by a preset pitch at a time point that occurs one period after the certain time point. The processor 350 may then compare a difference between the measured positions of the object with the preset pitch to thereby quantify a correction possibility for a reconstruction image. These operations will be described in more detail below with reference to FIGS. 7A, 7B, and 8.

The processor 350 may determine whether to perform correction on a reconstruction image by using the calculated correction possibility. For example, when the calculated correction possibility is high, the processor 350 may determine that the correction is to be performed automatically. Otherwise, when the calculated correction possibility is low, the processor 350 may control another CT imaging to be performed instead of performing image correction.

According to an embodiment of the disclosure, the processor 350 may determine whether to perform correction by comparing a calculated correction possibility with a given threshold. For example, when a calculated correction possibility is less than a preset threshold, the processor 350 may determine that correction is not to be performed. Furthermore, the processor 350 may determine that correction is to be performed only when the calculated correction possibility exceeds the preset threshold.

According to an embodiment of the disclosure, the processor 350 may derive a preset parameter value from a CT image reconstructed by the image processor 340 from X-ray projection image, set a region on which correction needs to be performed by using the derived preset parameter value, and perform correction on the set region automatically. The preset parameter value for the CT image may include at least one of a sharpness value or an entropy value. The processor 350 may measure at least one of a sharpness value or an entropy value in a reconstruction image and specify a region to be corrected in the reconstruction image by using the measured at least one of the sharpness value or the entropy value. Furthermore, the processor 350 may automatically perform correction on the specified region to be corrected.

The CT apparatus 300 may receive a correction possibility result value with respect to a parameter from a user. In this case, the processor 350 may train a correlation between the received correction possibility result value and the parameter by using machine learning. According to an embodiment of the disclosure, the processor 350 may update an equation used to calculate a correction possibility based on the trained correlation. Embodiments of the disclosure in which the processor 350 trains the correlation between a correction possibility result value and a parameter by using machine learning will be described in more detail below with reference to FIGS. 10A through 10C and 11.

The display 360 may display a reconstruction image and motion artifacts measured in the reconstruction image, as well as a correction possibility value calculated with respect to the motion artifacts. The display 360 may be constituted by a physical device including at least one of a cathode ray tube (CRT) display, a liquid crystal display (LCD), a plasma display panel (PDP), an organic light-emitting display (OLED), a field emission display (FED), a light-emitting diode (LED) display, a vacuum fluorescent display (VFD), a digital light processing (DLP) display, a flat panel display (FPD), a 3D display, or a transparent display, but is not limited thereto. According to an embodiment of the disclosure, the display 360 may formed as a touch screen including a touch interface.

When the display 360 is formed as a touch screen, the display 360 may receive a user touch input of setting a region where motion artifacts occur in a reconstruction image, i.e., a region to be corrected.

According to an embodiment of the disclosure, the display 360 may display a color mapping image obtained by mapping onto a reconstruction image a color corresponding to a correction possibility, i.e., a correction probability value, calculated by the processor 350, as described in more detail with reference to FIG. 13.

According to another embodiment of the disclosure, when the processor 350 determines that correction is to be performed, the display 360 may display a user interface (UI) indicating the expected time required to perform the correction, as described in more detail with reference to FIG. 14.

According to another embodiment of the disclosure, the display 360 may display parallel images respectively obtained before and after performing correction on a reconstruction image, as described in more detail below with reference to FIG. 15.

The CT apparatus 300 is configured to detect motion artifacts that occur due to a patient's motion during CT imaging from an X-ray projection image or a reconstruction image and quantify and display a correction possibility for the reconstruction image, thereby providing a basis for performing a quick determination as to whether to perform another CT imaging or to perform correction by removing the motion artifacts. Thus, user convenience may be increased. Furthermore, the time needed for correction may be reduced by selectively performing correction on only a portion having motion artifacts in a reconstruction image. This may be particularly useful in emergency situations, surgeries, or patients with serious illness.

Figure 4:
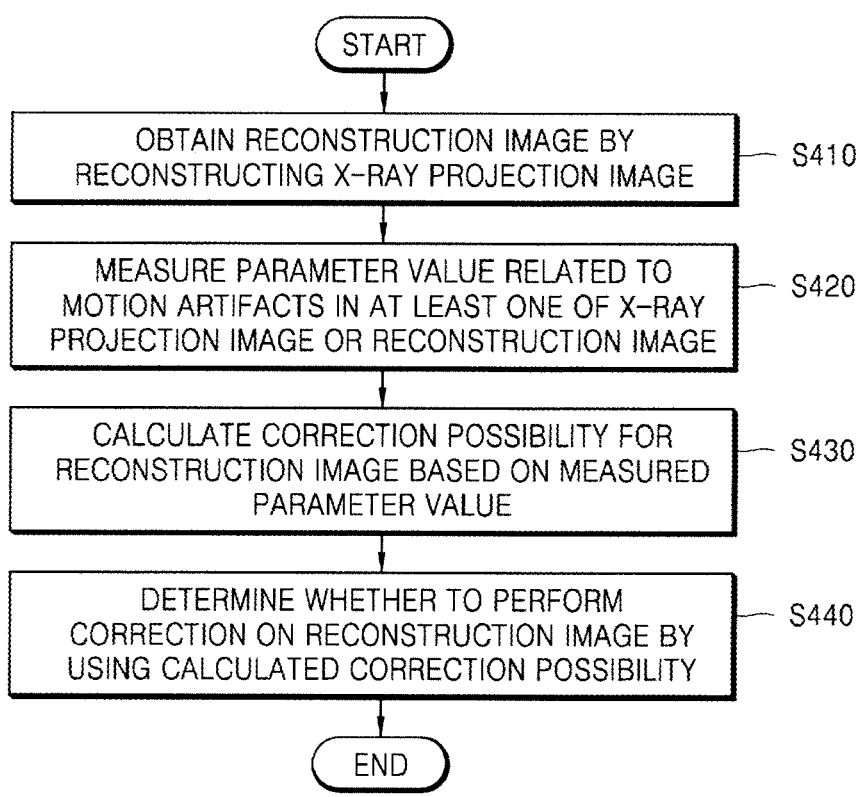
FIG. 4 is a flowchart of a method, performed by a CT apparatus, of calculating a correction possibility for a reconstruction image and determining whether to perform correction on the reconstruction image based on the calculated correction possibility, according to an embodiment of the disclosure.

FIG. 4 is a flowchart of a method, performed by a CT apparatus, of calculating a correction possibility for a reconstruction image and determining whether to perform correction on the reconstruction image based on the calculated correction possibility, according to an embodiment of the disclosure.

The CT apparatus obtains a reconstruction image by reconstructing an X-ray projection image (S410). The CT apparatus may emit X-rays toward an object via the X-ray source (310 of FIG. 3) and detect the X-rays that have passed through the object by using the X-ray detector (320 of FIG. 3). The CT apparatus may generate an X-ray projection image by using signals corresponding to the detected X-rays. Furthermore, according to an embodiment of the disclosure, the CT apparatus may reconstruct a CT image from the X-ray projection image by using FBP or an iterative method. However, embodiments are not limited thereto, and a CT image may be reconstructed from the X-ray projection image by using other known reconstruction methods.

The CT apparatus measures a parameter value related to motion artifacts in at least one of the X-ray projection image or the reconstruction image (S420). The CT apparatus may measure a parameter value related to motion artifacts, e.g., at least one of a sharpness value or an entropy value in the reconstruction image. According to an embodiment of the disclosure, the CT apparatus may measure a sharpness value in the reconstruction image by using at least one of total variation, $L_2$-norm for gradient, negative variance, or gradient variance, but embodiments of the disclosure are not limited thereto. Furthermore, the CT apparatus may measure an entropy value in the reconstruction image.

According to an embodiment of the disclosure, the CT apparatus may measure a parameter value related to motion artifacts in the X-ray projection image used in operation S410. For example, the CT apparatus may measure pieces of position information of a specific edge in a plurality of X-ray projection images acquired at different time points. The CT apparatus may acquire the pieces of position information of the specific edge measured in the X-ray projection images and quantify a difference between the acquired pieces of position information.

The CT apparatus calculates a correction possibility for the reconstruction image based on the measured parameter value (S430). According to an embodiment of the disclosure, the CT apparatus may calculate a correction possibility for the reconstruction image by quantifying at least one of a sharpness value or an entropy value measured in the reconstruction image. The CT apparatus may store an equation that is used to calculate a correction possibility for the reconstruction image by quantifying the parameter value measured in the reconstruction image, i.e., at least one of a sharpness value or an entropy value.

According to an embodiment of the disclosure, the CT apparatus may calculate a correction possibility by using position information measured with respect to an X-ray projection image. The CT apparatus emits X-rays toward the object via the X-ray source 310 as the X-ray source 310 rotates on a rotating frame for one period and emits X-rays toward the object again after the object is moved by a preset pitch. In this case, a difference between positions of a specific edge of the object, which are measured in a plurality of X-ray projection images acquired at different time points, has to be equal to the preset pitch. However, when motion artifacts occur due to movement of the object, the difference between positions of the specific edge in the X-ray projection images acquired at different time points may be greater than the pitch. In this way, the CT apparatus may compare a difference between positions of a specific edge measured in X-ray projection images acquired at different time points with a preset pitch and quantify a correction possibility based on a result of the comparing.

The CT apparatus determines whether to perform correction on the reconstruction image by using the calculated correction possibility (S440). According to an embodiment of the disclosure, the CT apparatus may calculate the correction possibility as a probability value. The CT apparatus may perform the correction on the reconstruction image only when the calculated correction possibility or probability value is high. Otherwise, when the calculated correction possibility or probability value is low, the CT apparatus may determine that another CT imaging is to be performed instead of the correction.

Figure 5A:
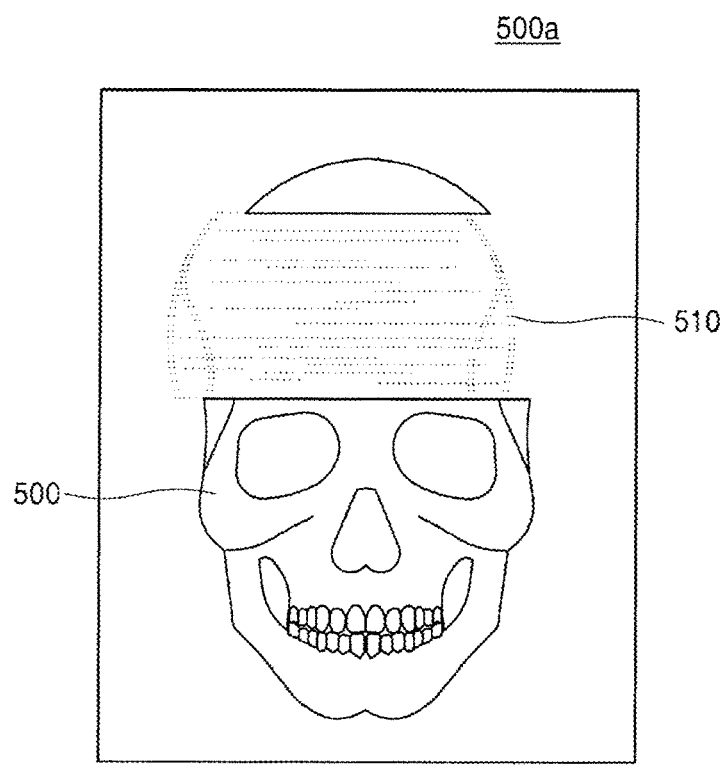
FIG. 5A illustrates a CT image in which motion artifacts occur due to movement of an object.

FIG. 5A illustrates a CT image 500a in which motion artifacts occur due to movement of an object. According to an embodiment of the disclosure, a CT apparatus may recognize a motion artifact area 510 of an image 500 of the object in the CT image 500a reconstructed from X-ray projection images.

Referring to FIG. 5A, the CT image 500a may include the image 500 that is captured of a head of a patient. The CT image 500a may further include the motion artifact area 510 exhibiting image distortion, blurring, degradation of image sharpness, etc., that occur due to patient movement during CT imaging. The motion artifact area 510 may have a sharpness value that is less than that of the other areas of the image 500.

The CT apparatus may measure at least one of a sharpness value or an entropy value in the CT image 500a.

For example, the CT apparatus may measure at least one of a mean sharpness value, a maximum sharpness value, a mean entropy value, or a maximum entropy value. According to an embodiment of the disclosure, the CT apparatus may measure a sharpness value with respect to each region in the CT image 500a by using at least one of total variation, L2-norm for gradient, negative variance, or gradient variance. The CT apparatus may calculate an average of sharpness values measured in the CT image 500a or specify a region having a maximum value among the measured sharpness values.

According to another embodiment of the disclosure, the CT apparatus may measure an entropy value of an image pixel in the CT image 500a. The measured entropy value means a degree of freedom or degree of disorder of pixel values in the CT image 500a, and an entropy value measured in the motion artifact area 510 may be higher than entropy values measured in the other areas of the image 500.

The CT apparatus may recognize, based on a measured parameter value, an area in which motion artifacts occur in the CT image 500a, i.e., a location of the motion artifact area 510. The CT apparatus may recognize the location of the motion artifact area 510 based on at least one of a sharpness value or an entropy value measured in the CT image 500a.

For example, the CT apparatus may recognize as the motion artifact area 510 an area in which at least one of a mean sharpness value, a maximum sharpness value, a mean entropy value, or a maximum entropy value is greater than thresholds respectively set with respect to image sharpness and entropy.

Furthermore, the CT apparatus may recognize the degree of image distortion in the motion artifact area 510 based on a difference between a sharpness value measured with respect to the CT image 500a and a threshold set with respect to image sharpness. Similarly, the CT apparatus may recognize the degree of image distortion in the motion artifact area 510 based on a difference between an entropy value measured in the CT image 500a and a threshold set with respect to entropy.

Figure 5B:
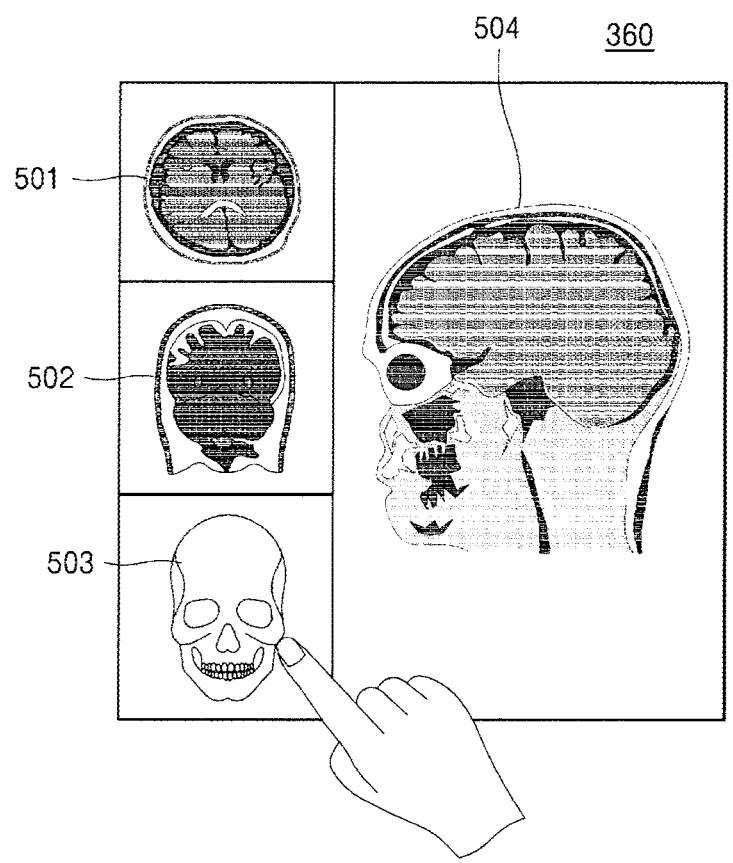
FIG. 5B is a diagram which illustrates a method of receiving a user input for selecting a region to be corrected in a CT image.

FIG. 5B illustrates a method of receiving a user input of selecting a region to be corrected in a CT image.

Referring to FIG. 5B, a display 360 of the CT apparatus may display a CT image in a plane oriented with respect to different axes of an object. For example, the display 360 may display a transaxial view image 501, a coronal view image 502, and a sagittal view image 504. The CT apparatus may display a 3D rendered image 503 of the object together on the display 360.

The CT apparatus may simultaneously display CT images in planes oriented with respect to different axes and receive a user input of selecting an area where image distortion, i.e., motion artifacts, occurs due to movement of an object in a CT image. According to an embodiment of the disclosure, the CT apparatus may receive a user input of setting a region to be corrected in a motion artifact area included in at least one of the transaxial view image 501, the coronal view image 502, the 3D rendered image 503, or the sagittal view image 504.

The CT apparatus may include a user inputter consisting of hardware components such as a keypad, a mouse, a touch pad, a touch screen, a trackball, a jog switch, etc. However, the user inputter is not limited to the above-described hardware components. In the embodiment shown in FIG. 5B, the display 360 of the CT apparatus may include a touch screen and receive a user touch input of selecting a region to be corrected from at least one of the transaxial view image 501, the coronal view image 502, the 3D rendered image 503, or the sagittal view image 504.

The CT apparatus may set a region to be corrected based on a received user input and measure a parameter value related to motion artifacts in the set region to be corrected. According to an embodiment of the disclosure, the CT apparatus may measure at least one of a sharpness value or an entropy value with respect to a region to be corrected, which is set according to a user input, and calculate a correction possibility for the region to be corrected based on the measured at least one of the sharpness value or the entropy value.

Figure 6:
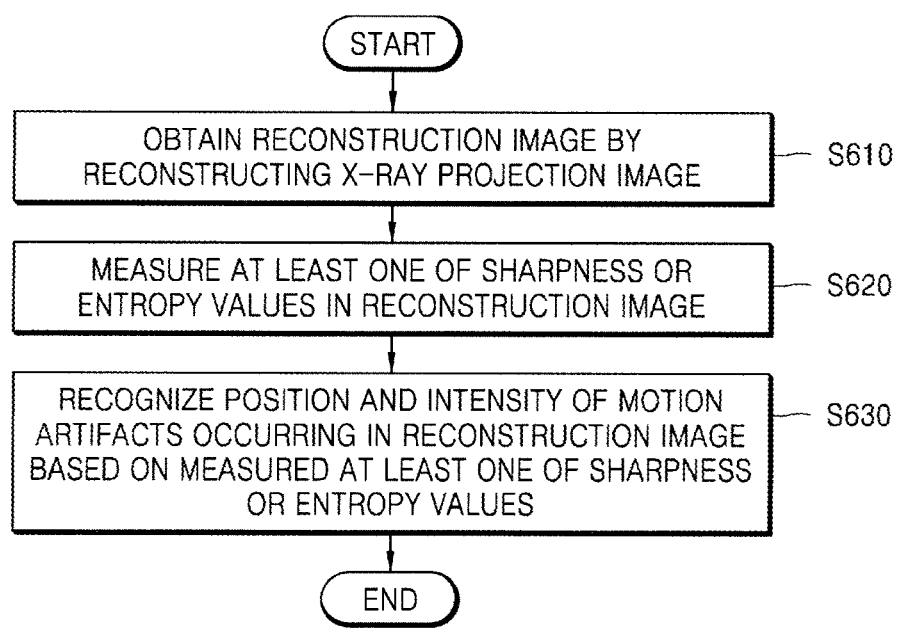
FIG. 6 is a flowchart of a method, performed by a CT apparatus, of recognizing a position and an intensity of motion artifacts occurring in a CT image, according to an embodiment of the disclosure.

FIG. 6 is a flowchart of a method, performed by a CT apparatus, of recognizing a position and an intensity of motion artifacts occurring in a CT image, according to an embodiment of the disclosure.

The CT apparatus obtains a reconstruction image by reconstructing a plurality of X-ray projection images (S610). According to an embodiment of the disclosure, the CT apparatus may emit X-rays toward an object and detect the X-rays that have passed through the object to thereby generate an X-ray projection image. Furthermore, the CT apparatus may reconstruct a CT image from the X-ray projection image by using FBP or an iterative method.

The CT apparatus measures at least one of a sharpness value or an entropy value in the reconstruction image (S620). According to an embodiment of the disclosure, the CT apparatus may measure a sharpness value in a reconstructed CT image by using at least one of total variation, L2-norm for gradient, negative variance, or gradient variance, but embodiments of the disclosure are not limited thereto. Furthermore, the CT apparatus may measure an entropy value in the reconstructed CT image.

According to an embodiment of the disclosure, the CT apparatus may calculate an average of sharpness values measured in a reconstruction image or specify a region having a maximum value among the measured sharpness values. Furthermore, the CT apparatus may calculate an average of entropy values of pixels in the reconstruction image or specify a pixel having a maximum value among the measured entropy values.

The CT apparatus recognizes a position and an intensity of motion artifacts occurring in the reconstruction image based on the measured at least one of the sharpness value or the entropy value (S630).

For example, the CT apparatus may recognize a location of an area in which motion artifacts occur in a reconstruction image based on at least one parameter from among a mean sharpness value, a maximum sharpness value, a mean entropy value, and a maximum entropy value.

The CT apparatus may recognize an intensity of motion artifacts by using at least one of a sharpness value or an entropy value measured in a reconstruction image. For example, the CT apparatus may recognize the intensity of motion artifacts based on a difference between a sharpness threshold and either a mean or maximum sharpness value measured in the reconstruction image. Furthermore, in another embodiment of the disclosure, the CT apparatus may recognize the intensity of motion artifacts based on a difference between an entropy threshold and either a mean or maximum entropy value measured in the reconstruction image.

Figure 7A:
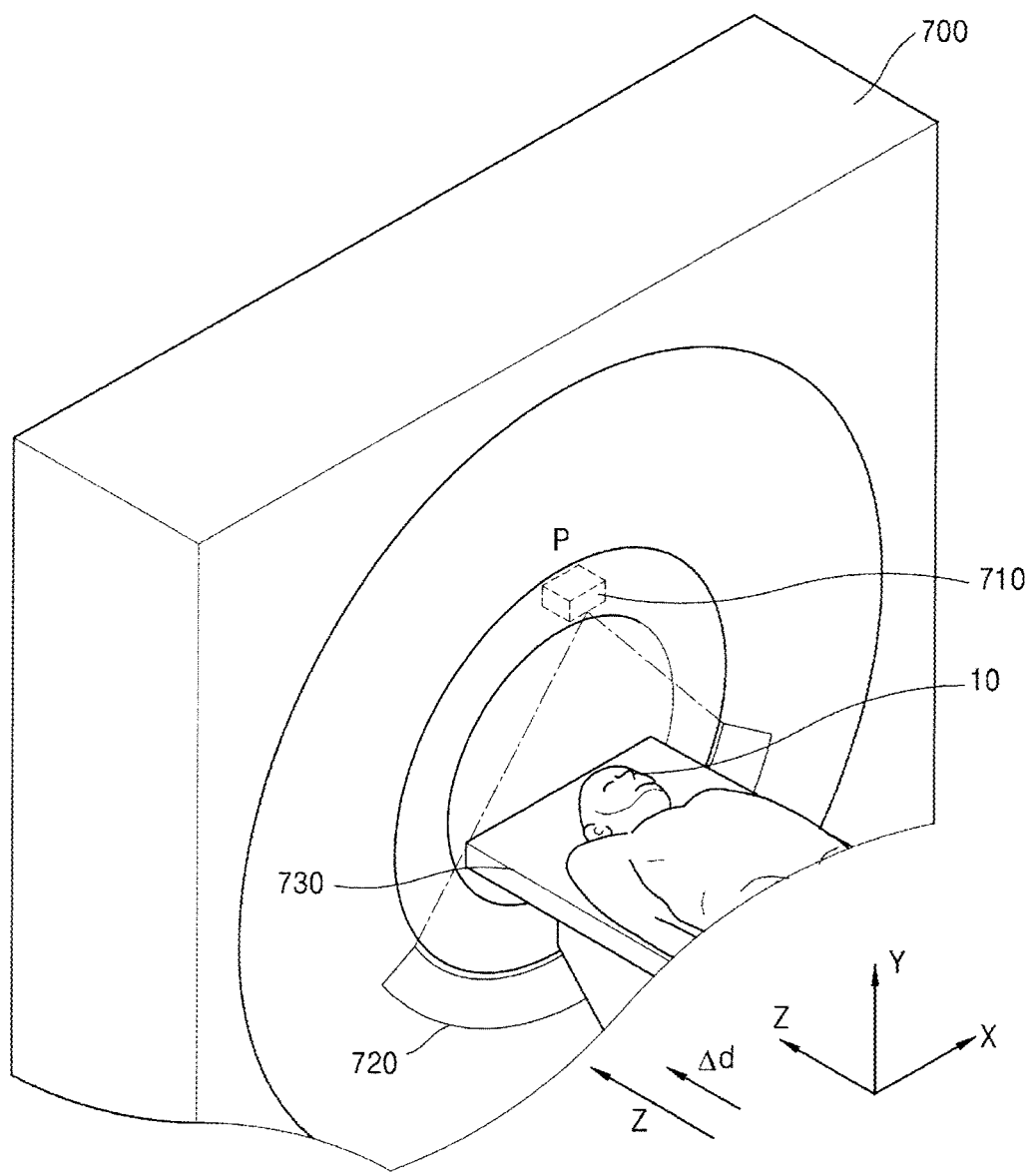
FIG. 7A is a diagram which illustrates a method, performed by a CT apparatus, of acquiring an X-ray projection image of an object and calculating a correction possibility for a reconstruction image based on position information of the object measured in the acquired X-ray projection image, according to an embodiment of the disclosure.
Figure 7B:
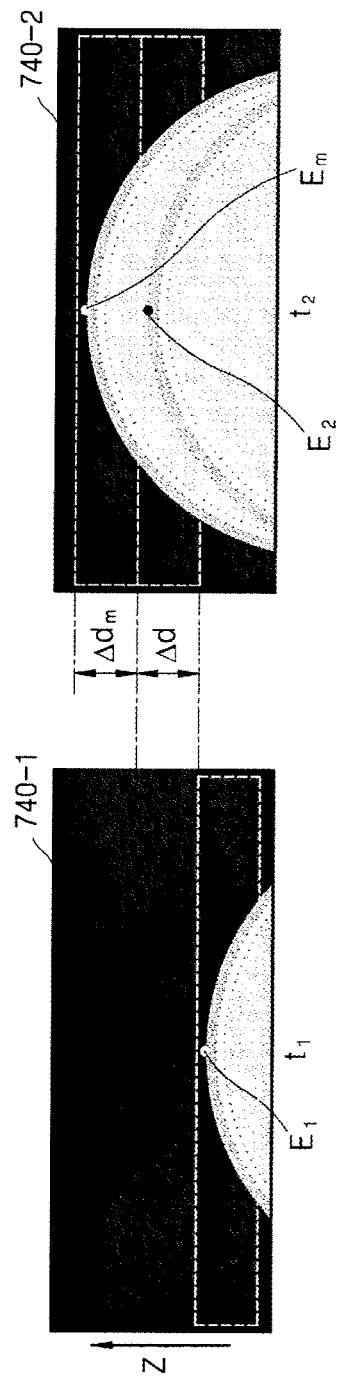
FIG. 7B is a diagram which illustrates a method, performed by a CT apparatus, of acquiring an X-ray projection image of an object and calculating a correction possibility for a reconstruction image based on position information of the object measured in the acquired X-ray projection image, according to an embodiment of the disclosure.

FIG. 7A illustrates a method, performed by a CT apparatus 700, of acquiring an X-ray projection image of an object and calculating a correction possibility for a reconstruction image based on position information of the object measured in the acquired X-ray projection image, according to an embodiment of the disclosure. FIG. 7B illustrates a method, performed by the CT apparatus 700, of acquiring an X-ray projection image of an object and calculating a correction possibility for a reconstruction image based on position information of the object measured in the acquired X-ray projection image, according to an embodiment of the disclosure.

Referring to FIG. 7A, the CT apparatus 700 may emit X-rays toward an object 10 via an X-ray source 710 while rotating the X-ray source 710 by a preset angle on a rotating frame with an axis disposed at a center of the object 10. An X-ray detector 720 may detect the X-rays that have passed through the object 10 to thereby acquire a plurality of X-ray projection images respectively corresponding to a plurality of angular positions at which the X-rays are emitted. According to an embodiment of the disclosure, after emitting the X-rays via the X-ray source 710 that rotates 360 degrees around the object 10, i.e., after a lapse of one period, the CT apparatus 700 may move a bed 730 on which the object 10 is placed by a pitch having a preset interval in a third (Z-axis) direction. By moving the bed 730 by the preset pitch, i.e., after moving the object 10 by a pitch $\Delta d$ in the third (Z-axis) direction, the CT apparatus 700 may emit X-rays toward the object 10 via the X-ray source 710 while rotating the X-ray source 710 by 360 degrees and acquire a plurality of X-ray projection images by detecting the X-rays that have passed through the object 10 via the X-ray detector 720. In other words, the CT apparatus 700 may acquire a plurality of X-ray projection images during a first period by emitting X-rays while rotating the X-ray source 710 from 0 to 360 degrees, and after moving the object 10 by a pitch by using the bed 730, acquire a plurality of X-ray projection images during a second period.

The CT apparatus 700 may analyze a position relation between specific edges in X-ray projection images acquired at a specific angular position, e.g., a 1-degree angular position from among a plurality of X-ray projection images respectively acquired during the first and second periods. Referring to FIG. 7B, a first X-ray projection image 740-1 may be an X-ray projection image of an object acquired at a specific angular position from among the X-ray projection images acquired during the first period. Furthermore, a second X-ray projection image 740-2 may be an X-ray projection image of the object acquired at the specific angular position from among the X-ray projection images acquired during the second period after a lapse of the first period. According to an embodiment of the disclosure, the first and second X-ray projection images 740-1 and 740-2 may be acquired by emitting X-rays at the same angular position. The first and second X-ray projection images 740-1 and 740-2 may be projection images obtained using a helical scan, but are not limited thereto.

The CT apparatus 700 may recognize a specific edge in an X-ray projection image and measure a position of the specific edge by using a known image processing techniques. According to an embodiment of the disclosure, the CT apparatus 700 may recognize a position of a first edge $E_1$ of the object in the first X-ray projection image 740-1 captured at a first time point $t_1$ and acquire position information of the first edge $E_1$. According to an embodiment of the disclosure, similarly, the CT apparatus 700 may acquire position information of a second edge $E_2$ of the object in the second X-ray projection image 740-2 captured at a second time point $t_2$. When there is no movement of the object, i.e., the patient, during the time between the first and second time points $t_1$ and $t_2$, a distance between the first and second edges $E_1$ and $E_2$ has to be equal to a pitch interval $\Delta d$ by which the bed (730 of FIG. 7A) moves. However, when the patient moves during the time between the first and second time points $t_1$ and $t_2$, i.e., during the transition from one period to the next, position information of an edge $E_m$ in the second X-ray projection image 740-2 may be different from predicted position information. In other words, when motion artifacts occur due to motion of the object during the time between the first and second time points $t_1$ and $t_2$, the position information of an edge in the second X-ray projection image 740-2 may be measured as $E_m$.

In the embodiment shown in FIG. 7B, a difference $\Delta d_m$ between a position of the edge $E_m$ measured after movement of the object and a position of the second edge $E_2$ measured when there is no movement of the object may be proportional to the degree of motion artifacts. Furthermore, because a greater difference $\Delta d_m$ means a larger movement of the object, a correction possibility in a CT image that is subsequently reconstructed by performing back-projection on the second X-ray projection image 740-2 may be inversely proportional to the difference $\Delta dm$. In other words, as the difference $\Delta d_m$ increases, a correction possibility for a reconstruction image, i.e., a correction probability value, may decrease.

According to an embodiment of the disclosure, the CT apparatus 700 may calculate a correction possibility for a CT image by quantifying a difference between the position of the edge $E_m$ when motion artifacts occur at the second time point $t_2$ and the position of the second edge $E_2$ when no motion artifacts occur at the same time point. Furthermore, the CT apparatus 700 may determine whether to perform another CT imaging or correction by comparing the recognized difference $\Delta d_m$ with a preset threshold. For example, when the difference $\Delta d_m$ is greater than the preset threshold, the CT apparatus 700 may determine that another CT imaging is to be performed instead of correction. Otherwise, when the difference $\Delta d_m$ is less than the preset threshold, the CT apparatus 700 may determine that correction is to be performed.

Figure 8:
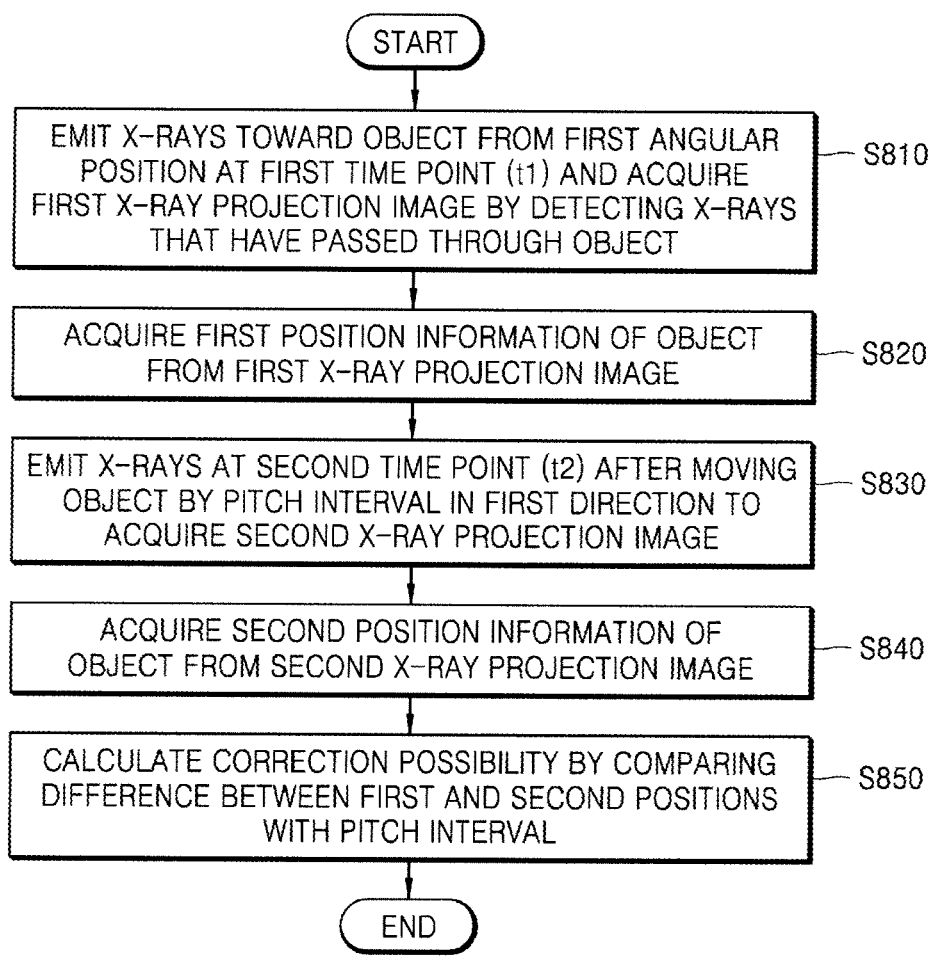
FIG. 8 is a flowchart of a method, performed by a CT apparatus, of acquiring an X-ray projection image of an object and calculating a correction possibility for a reconstruction image based on position information of the object measured in the acquired X-ray projection image, according to an embodiment of the disclosure.

FIG. 8 is a flowchart of a method, performed by a CT apparatus, of acquiring an X-ray projection image of an object and calculating a correction possibility for a reconstruction image based on position information of the object measured in the acquired X-ray projection image, according to an embodiment of the disclosure.

The CT apparatus may emit X-rays toward the object via an X-ray source while rotating the X-ray source on a rotating frame having the object as a central axis and acquire a plurality of X-ray projection images by detecting the X-rays that have passed through the object via an X-ray detector. The CT apparatus emits X-rays toward an object from a first angular position at a first time point $t_1$ and acquires a first X-ray projection image by detecting the X-rays that have passed through the object (S810).

The CT apparatus acquires first position information of the object from the first X-ray projection image (S820). According to an embodiment of the disclosure, the CT apparatus may recognize an edge of the object in the first X-ray projection image by using a known image processing technique and measure a position of the recognized edge. The CT apparatus may store information of the measured position by using a coordinate system.

After moving the object by a pitch interval in a first direction, the CT apparatus emits X-rays toward the object at a second time point $t_2$ to acquire a second X-ray projection image (S830). According to an embodiment of the disclosure, after acquisition of the first X-ray projection image, the CT apparatus may move the object by a pitch having a preset interval in a Z-axis direction. After moving the object, the CT apparatus may emit X-rays toward the object via the X-ray source and acquire a second X-ray projection image at the same angular position where the first X-ray projection image is acquired.

The CT apparatus acquires second position information of the object from the second X-ray projection image (S840). According to an embodiment of the disclosure, the CT apparatus may recognize an edge of the object in the second X-ray projection image and measure a position of the recognized edge. The CT apparatus may store the second position information of the edge measured in the second X-ray projection image by using a coordinate system. The edge recognized in operation S840 may be the same as the edge recognized in operation S820. When there is no movement of the object during acquisition of an X-ray projection image via emission of X-rays, a coordinate value difference between the first position information and the second position information respectively measured in operations S820 and S840 is equal to the pitch interval by which the object moves in operation S830. Otherwise, when the object moves during acquisition of the X-ray projection image, the coordinate value difference between the first position information and the second position information may be greater than the pitch interval.

The CT apparatus calculates a correction possibility by comparing a difference between first and second positions with the pitch interval (S850). According to an embodiment of the disclosure, the CT apparatus may calculate a coordinate value difference between the first position information acquired in operation S820 and the second position information acquired in operation S840, and compare the coordinate value difference with a pitch interval. The CT apparatus may calculate a difference between the pitch interval and a calculated coordinate difference between first and second positions and quantify a correction possibility as a probability value. The difference between the coordinate difference and the pitch interval may be inversely proportional to the correction possibility. For example, as the difference between the coordinate value difference and the pitch interval increases, the correction possibility, i.e., a correction probability value, may decrease.

According to the embodiments of the disclosure shown in FIGS. 7A, 7B, and 8, the CT apparatus may determine a correction possibility based on analysis of a position of an edge in an X-ray projection image before generating a CT image by reconstructing at least one X-ray projection image. Thus, by determining the correction possibility, it is possible to shorten the time required to reconstruct the CT image.

Figure 9:
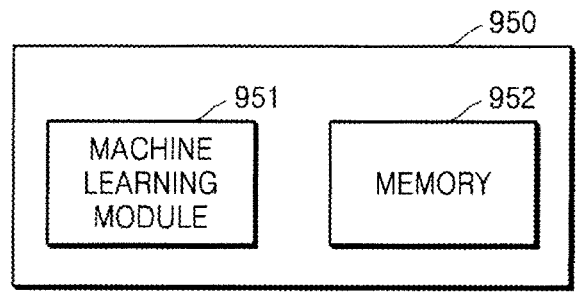
FIG. 9 is a block diagram illustrating components of a CT apparatus according to an embodiment of the disclosure.

FIG. 9 is a block diagram illustrating components of a CT apparatus according to an embodiment of the disclosure. Referring to FIG. 9, the CT apparatus may include a processor 950. The processor 950 may correspond to the processor 350 described with reference to FIG. 3 except for the following configuration and operation.

The processor 950 may include a machine learning module 951 and a memory 952. The CT apparatus may receive from a user a result value for correction that has been already performed on a reconstruction image with motion artifacts. A correction result value may be a numerical value obtained when the user estimates, scores, and quantifies the degree to which correction has been made with respect to a probability value obtained by calculating a correction possibility for a reconstruction image based on a parameter related to motion artifacts. The CT apparatus may receive a correction result value via a user inputter and store the same in the memory 952.

The machine learning module 951 may train a correction result value based on artificial intelligence (AI). For example, the machine learning module 951 may train a correlation between a correction result value and each parameter value related to motion artifacts by using at least one machine learning algorithm from among linear regression, logistic regression, decision tree, random forest, support vector machine (SVM), Naïve Bayes, k-nearest neighbors (KNN), or artificial neural network (ANN). However, the above-described machine learning algorithms are merely an example, and the machine learning module 951 may use any machine learning algorithm known in the field of AI technology.

According to an embodiment of the disclosure, the machine learning module 951 may classify correction result values received from the user respectively according to a sharpness value and an entropy value and train a correlation between either a sharpness or entropy value and its corresponding correction result value. For example, the machine learning module 951 may classify correction result values based on at least one of parameter values, i.e., at least one of a mean sharpness value, a maximum sharpness value, a mean entropy value, or a maximum entropy value and train a correlation between each of the parameter values and its corresponding correction result value.

According to an embodiment of the disclosure, the machine learning module 951 may be composed of a hardware unit having computational capabilities of training a correction result value received from the user and using the trained correction result value as feedback data in calculating a correction possibility. For example, the machine learning module 951 may be constituted by at least one of a CPU, a microprocessor, a graphics processing unit, or any combination thereof.

The memory 952 may store a parameter value related to motion artifacts in a CT image and an equation used to calculate a correction possibility based on a parameter. According to an embodiment of the disclosure, the memory 952 may store a threshold preset with respect to the parameter. For example, the memory 952 may be composed of a non-volatile memory such as dynamic random access memory (DRAM), static RAM (SRAM), synchronous DRAM (SDRAM), or the like. However, embodiments are not limited thereto, and the memory 952 may be composed of a non-volatile memory including at least one of one time programmable read-only memory (OTPROM), programmable ROM (PROM), erasable and programmable ROM (EPROM), electrically erasable and programmable (EEPROM), mask ROM, flash ROM, a hard disk drive (HDD), or a solid state drive (SSD). When the memory 952 is a non-volatile memory, the memory 952 may not be included in the processor 950 but be included as a component of the CT apparatus.

According to an embodiment of the disclosure, the memory 952 may store a correction result value received from the user. In another embodiment of the disclosure, the CT apparatus may include an internal or external database for storing a correction result value.

According to an embodiment of the disclosure, the machine learning module 951 may train a correlation between either image sharpness or entropy that is a parameter related to motion artifacts in a CT image and a correction result value stored in the memory 952. The machine learning module 951 may also update an equation used to calculate a correction possibility based on the trained correlation, as described in more detail below with reference to FIGS. 10A through 10C.

Figure 10A:
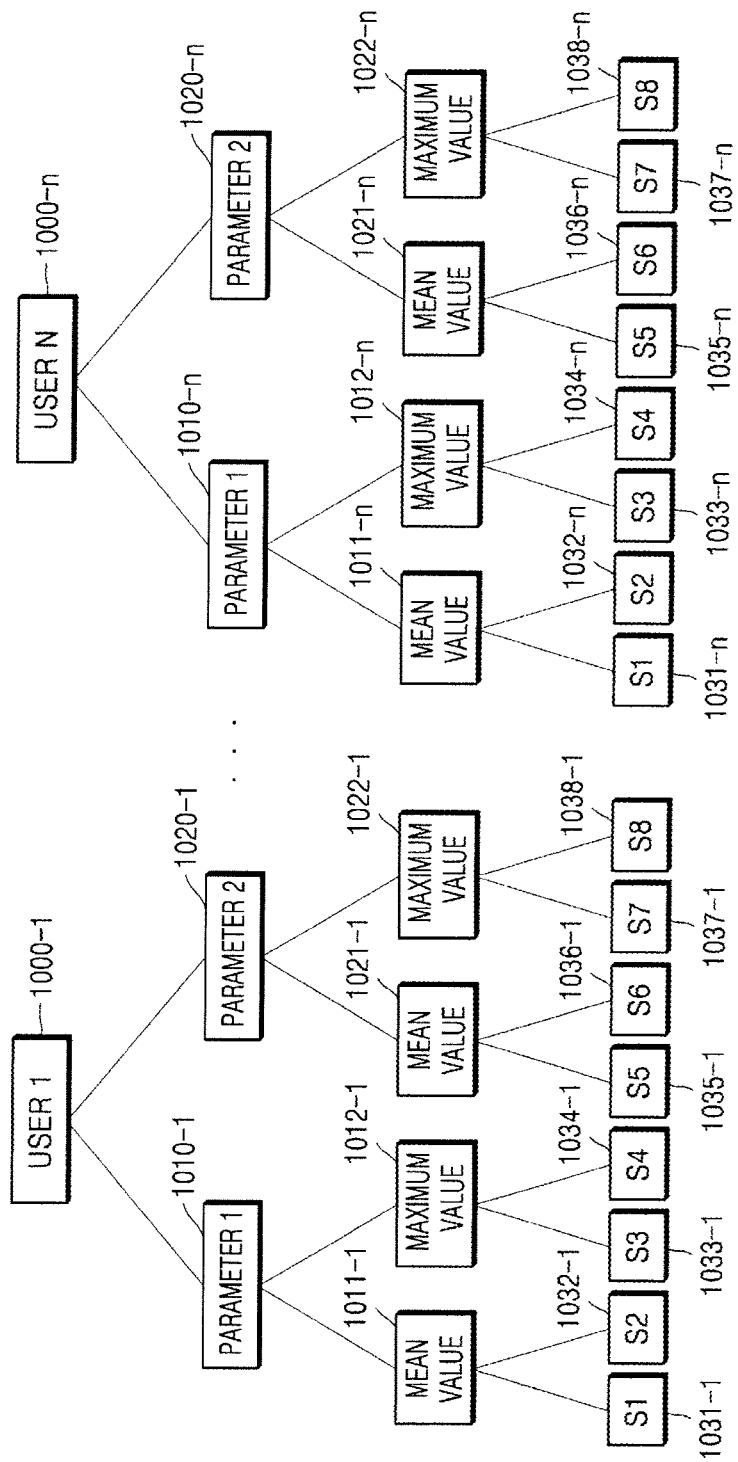
FIG. 10A is a diagram which illustrates a method, performed by a CT apparatus, of training a correction possibility result value received from a user by using a machine learning algorithm and updating an equation used to calculate a correction possibility by using the trained correction possibility result value as feedback data, according to an embodiment of the disclosure.

FIG. 10A illustrates a method, performed by a CT apparatus, of training a correction result value received from a user by using a machine learning algorithm and updating an equation used to calculate a correction possibility by using the trained correction result value as feedback data, according to an embodiment of the disclosure.

Referring to FIG. 10A, the CT apparatus may train a correlation between a correction result value received from each of a plurality of users and each of a plurality of parameters related to motion artifacts by using a machine learning module. In the embodiment of the disclosure shown in FIG. 10A, the machine learning module may classify correction result values 1031-1 through 1038-1 and 1031-n through 1038-n respectively received from a first user 1000-1 and an n-th user 1000-n by using a decision tree method.

The machine learning module may receive correction result values 1031-1 through 1031-8 from the first user 1000-1 and classify the received correction result values 1031-1 through 1031-8 according to mean values (1011-1 and 1021-1) of first and second parameters 1010-1 and 1020-1 and maximum values (1012-1 and 1022-1) thereof. According to an embodiment of the disclosure, the first parameter 1010-1 may be image sharpness of a CT image, and the second parameter 1020-1 may be an entropy value of pixels included in the CT image. However, this is merely an example, and the first and second parameters 1010-1 and 1020-1 may be other parameters related to motion artifacts.

According to an embodiment of the disclosure, the machine learning module may classify correction result values 1031-1 and 1032-1 according to the first parameter 1010-1, i.e., a mean sharpness value 1011-1 and correction result values 1033-1 and 1034-1 according to a maximum sharpness value 1012-1. By doing so, the machine learning module may train a correlation between the mean sharpness value 1011-1 and the correction result values 1031-1 and 1032-1 and a correlation between the maximum sharpness value 1012-1 and the correction result values 1033-1 and 1034-1. Similarly, the machine learning module may classify correction result values 1035-1 and 1036-1 according to the second parameter 1020-1, i.e., a mean entropy value 1021-1 and correction result values 1037-1 and 1038-1 according to a maximum entropy value 1022-1. By doing so, the machine learning module may train a correlation between the mean entropy value 1021-1 and the correction result values 1035-1 and 1036-1 and a correlation between the maximum entropy value 1022-1 and the correction result values 1037-1 and 1038-1. Although it has been described that the machine learning module trains correction result values based on mean and maximum values of the first and second parameters 1010-1 and 1020-1, this is merely an example. According to an embodiment of the disclosure, the machine learning module may train correction result values by using maximum, minimum, mean, and median sharpness values or maximum, minimum, mean, and median entropy values.

The machine learning module may train a correlation between a correction result value and a parameter for each of the first through n-th users 1000-1 through 1000-n and update an equation used to calculate a correction possibility by applying the trained correlation as feedback data.

Figure 10B:
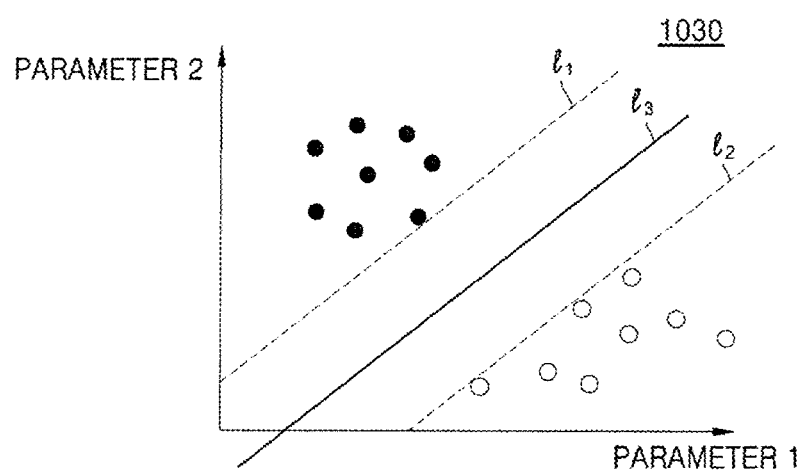
FIG. 10B is a graph which illustrates a method, performed by a machine learning module, of training a correlation between a parameter related to motion artifacts in a CT image and a correction result value received from a user by using an SVM algorithm, according to an embodiment of the disclosure.

FIG. 10B illustrates a method, performed by a machine learning module, of training a correlation between a parameter related to motion artifacts in a CT image and a correction result value received from a user by using a Support Vector Machine (SVM) algorithm.

Referring to FIG. 10B, the machine learning module may represent a correlation between a correction result value received from the user and either first or second parameter with a graph 1030 by using an SVM algorithm. According to an embodiment of the disclosure, the first parameter may be a sharpness value of a CT image, and the second parameter may be an entropy value of pixels in the CT image. However, embodiments of the disclosure are not limited thereto.

According to a method of training a correction result value via SVM, the machine learning module may divide correction result values, i.e., values indicated by white and black circles, into two groups, measure a distance between correction result values respectively in the two groups to find two centers of the distance respectively, and determine an optimal hyper line in the midway between the two centers. The machine learning module may find a pipe by drawing virtual lines l1 and l2 with respect to two groups respectively composed of correction result values indicated by white and black circles and then determine an optimal hyper plane by drawing a new line l3 within the pipe. In this case, the optimal hyper line may be determined by satisfying constraints that correction result values may not exist between the two virtual lines l1 and l2 and the optimal hyper line maximizes a margin that is a distance between the two virtual lines l1 and l2.

By using the method, the machine learning module may train a correlation between either first or second parameter related to motion artifacts and a correction result value and update an equation used to calculate a correction possibility by applying the trained correlation as feedback data.

When a correlation between a correction result value and a parameter value is trained using the SVM method described with reference to FIG. 10B, the result of such training may not be accurate because the correction result value has non-linear features. FIG. 10C illustrates an SVM method whereby a feature map 1060 is obtained by multiplying a kernel function 1050 by a graph 1040 of correction result values pre-classified according to first and second parameters.

Referring to FIG. 10C, the machine learning module may map the kernel function 1050 into the graph 1040 obtained by classifying correction result values received from the user according to the first and second parameters related to motion artifacts. According to an embodiment of the disclosure, the machine learning module may train a correlation between a correction result value and either sharpness or entropy of a reconstruction image via the obtained feature map 1060 and update an equation used to calculate a correction possibility by applying the trained correlation as feedback data.

According to the embodiments of the disclosure shown in FIGS. 10A through 10C, the CT apparatus is configured to train a correction result value received from the user based on machine learning and update an equation used to calculate a correction possibility by inputting the trained result as feedback data, thereby providing an improved accuracy in calculating a correction possibility.

Figure 11:
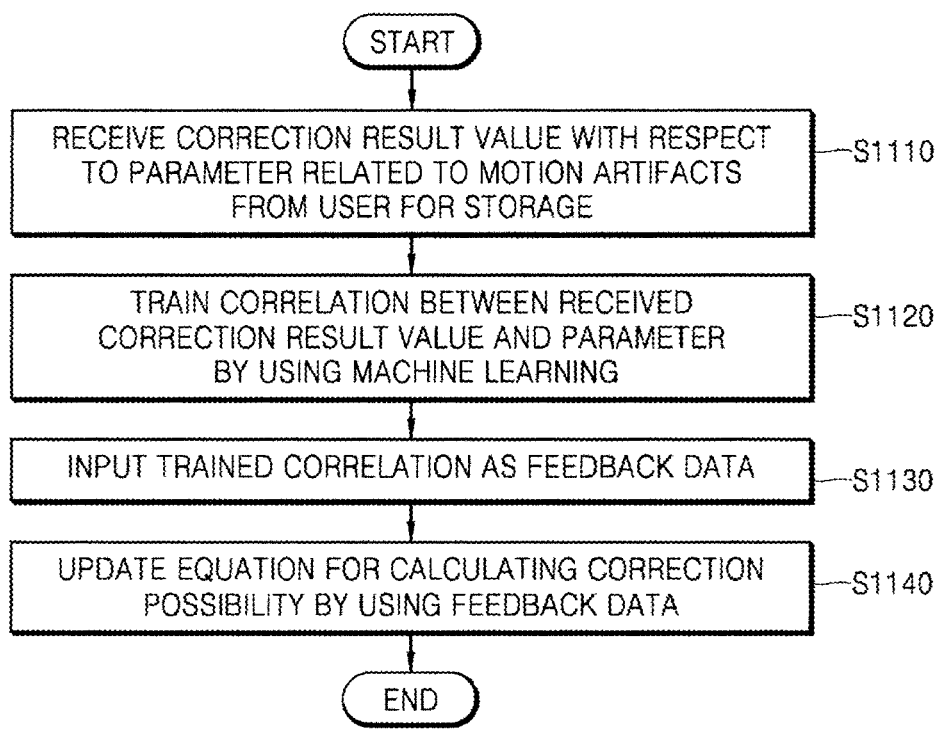
FIG. 11 is a flowchart of a method, performed by a CT apparatus, of training a correction possibility result value received from a user by using a machine learning algorithm and updating an equation used to calculate a correction possibility by using the trained correction possibility result value as feedback data, according to an embodiment of the disclosure.

FIG. 11 is a flowchart of a method, performed by a CT apparatus, of training a correction result value received from a user by using a machine learning algorithm and updating an equation used to calculate a correction possibility by using the trained correction result value as feedback data, according to an embodiment of the disclosure.

The CT apparatus receives a correction result value with respect to a parameter related to motion artifacts from the user and stores the received correction result values (S1110). A correction result value may be a numerical value obtained when the user estimates, scores, and quantifies the degree to which correction has been made with respect to a probability value obtained by calculating a correction possibility for a reconstruction image based on a parameter related to motion artifacts. The CT apparatus may receive correction result values from a plurality of users and store the same in a memory. According to an embodiment of the disclosure, parameter values related to motion artifacts may be sharpness and entropy values of a reconstruction image.

The CT apparatus trains a correlation between the received correction result value and the parameter by using machine learning (S1120). The CT apparatus may train the correction result value based on AI. For example, the CT apparatus may train a correlation between a correction result value and each parameter value related to motion artifacts by using at least one machine learning algorithm from among linear regression, logistic regression, decision tree, random forest, SVM, Naïve Bayes, KNN, or ANN.

The CT apparatus may classify correction result values according to parameters including at least one of mean, maximum, minimum, and median sharpness values or mean, maximum, minimum, and median entropy values and train a correlation between each of the parameter values and its corresponding correction result value.

The CT apparatus may input the trained correlation as feedback data (S1130).

The CT apparatus updates an equation used to calculate a correction possibility by using the feedback data (S1140). According to an embodiment of the disclosure, the CT apparatus may update, by using the feedback data, an equation used to calculate a correction possibility based on image sharpness and entropy prestored in the memory.

In another embodiment of the disclosure, the CT apparatus may receive the correlation between the correction result value and either image sharpness or correction result value as feedback data and update thresholds respectively set with respect to image sharpness and entropy prestored in the memory.

Figure 12:
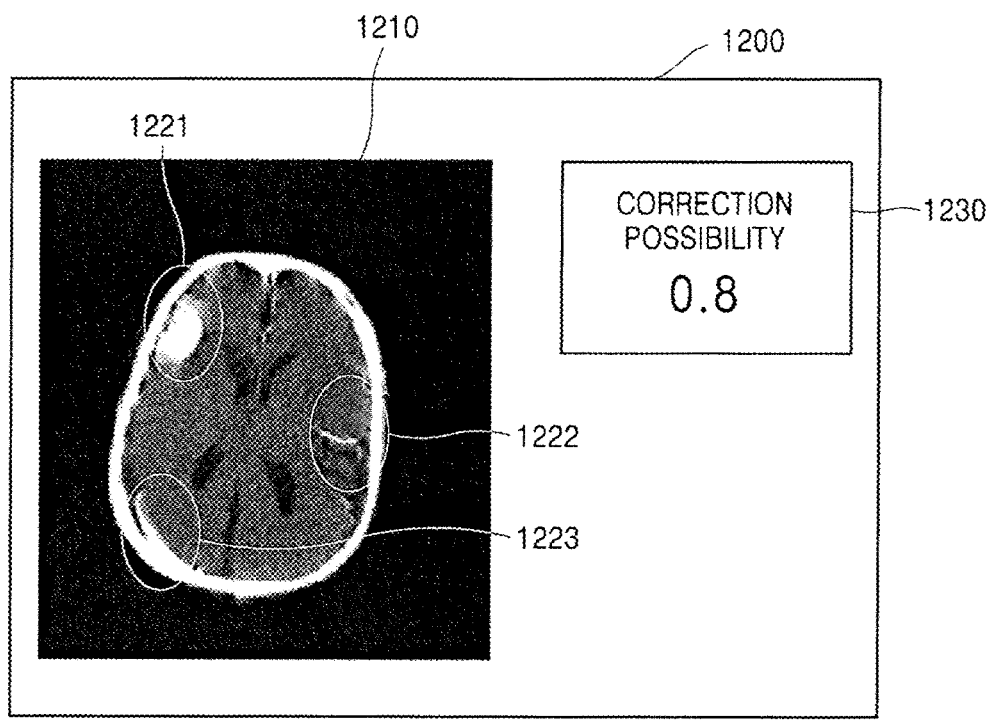
FIG. 12 is a diagram which illustrates an example of user interface (UI) of a CT apparatus that displays a reconstruction image and a UI indicating a correction possibility in the reconstruction image, according to an embodiment of the disclosure.

FIG. 12 illustrates an example of a UI of a CT apparatus that displays a reconstruction image 1210 and a UI 1230 indicating a correction possibility in the reconstruction image 1210, according to an embodiment of the disclosure.

Referring to FIG. 12, a display 1200 of the CT apparatus may display the reconstruction image 1210 into which motion artifacts are introduced due to movement of an object during CT imaging and the UI 1230 indicating a correction possibility for the reconstruction image 1210. According to an embodiment of the disclosure, the reconstruction image 1210 may be a CT image reconstructed from an X-ray projection image acquired by emitting X-rays toward the object and detecting the X-rays that have passed through the object. The reconstruction image 1210 may have motion artifacts 1221, 1222, and 1223 including image blurs and distortions induced due to movement of the object during CT imaging.

The display 1200 may display the UI 1230 indicating a correction possibility calculated by measuring at least one of a sharpness value or an entropy value of each of the motion artifacts 1221, 1222, and 1223. According to an embodiment of the disclosure, the CT apparatus may receive a user input of selecting a region in which one of the motion artifacts 1221, 1222, and 1223 occur in the reconstruction image 1210, and the display 1200 may display a correction possibility in the region selected according to the received user input.

Figure 13:
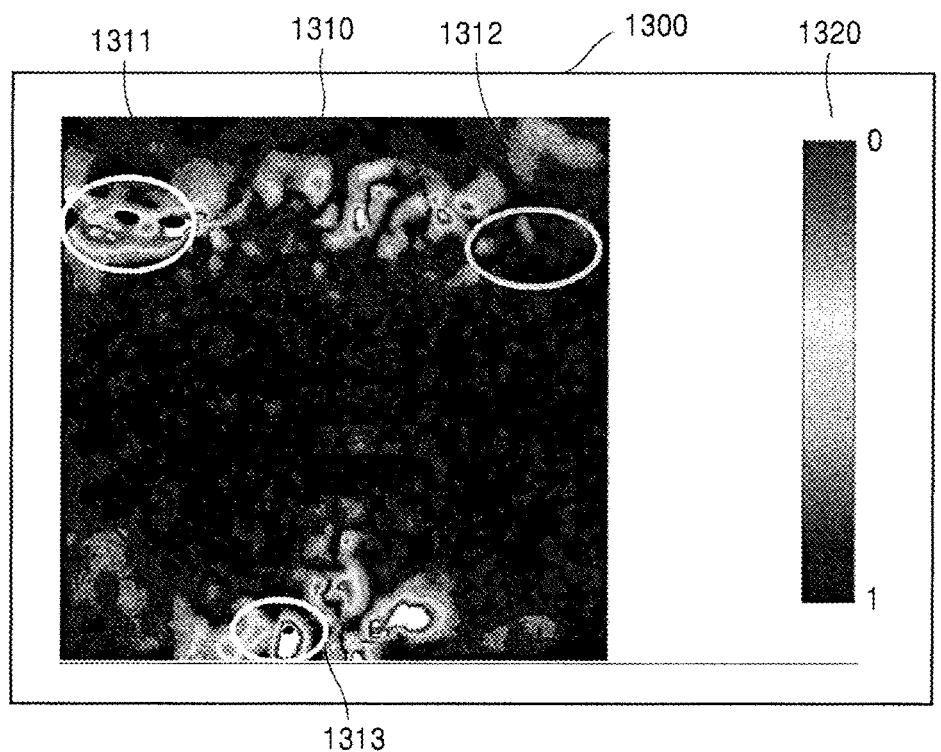
FIG. 13 is a diagram which illustrates an example of a screen on which a CT apparatus displays a correction possibility in a reconstruction image by mapping a correction possibility value to colors, according to an embodiment of the disclosure.

FIG. 13 illustrates an example of a screen on which a CT apparatus displays a correction possibility in a reconstruction image by mapping a correction possibility value to colors, according to an embodiment of the disclosure.

Referring to FIG. 13, the CT apparatus may display a color mapping image 1310 obtained by color-coding correction possibility values of pixels in the reconstruction image (CT image) on a display 1300. The display 1300 may display not only the color mapping image 1310 but also a color bar 1320 indicating correction possibility values corresponding to respective colors on the right side of the color mapping image 1310. Colors displayed on the color bar 1320 may respectively correspond to correction possibility values for the CT image, i.e., a correction probability value. According to an embodiment of the disclosure, 0 and 1 respectively displayed at the top and bottom of the color bar 1320 may indicate correction probability values.

As seen on the color bar 1320, as a correction probability value decreases due to a higher intensity of motion artifacts, i.e., as a corresponding color moves to the top of the color bar 1320, the corresponding color may become closer to a red color. Furthermore, when a correction probability value is high due to a low intensity of motion artifacts, a corresponding color may be shown as a blue color displayed at the bottom of the color bar 1320. However, this is merely an example, and color mapping is not limited to the example shown in FIG. 13.

A first region 1311 has low image sharpness due to a relatively severe level of blur among regions having motion artifacts in the color mapping image 1310. Thus, because the first region 1311 has a low correction possibility, i.e., a low correction probability value, the first region 1311 may be indicated in a red color compared to the other regions. On the other hand, a third region 1313 having fewer portions in red than the first region 1311 may have a higher correction possibility than the first region 1311. The second region 1312 having more portions in blue than the first and third regions 1311 and 1313 suffers from little motion artifacts and may have a high correction possibility.

In the embodiment shown in FIG. 13, the CT apparatus may display a color possibility value corresponding to motion artifacts that occur in pixels in the CT image by mapping the color possibility value to colors, thereby allowing the user to quickly identify a region having motion artifacts and a correction possibility for the region and accordingly improving user convenience.

Figure 14:
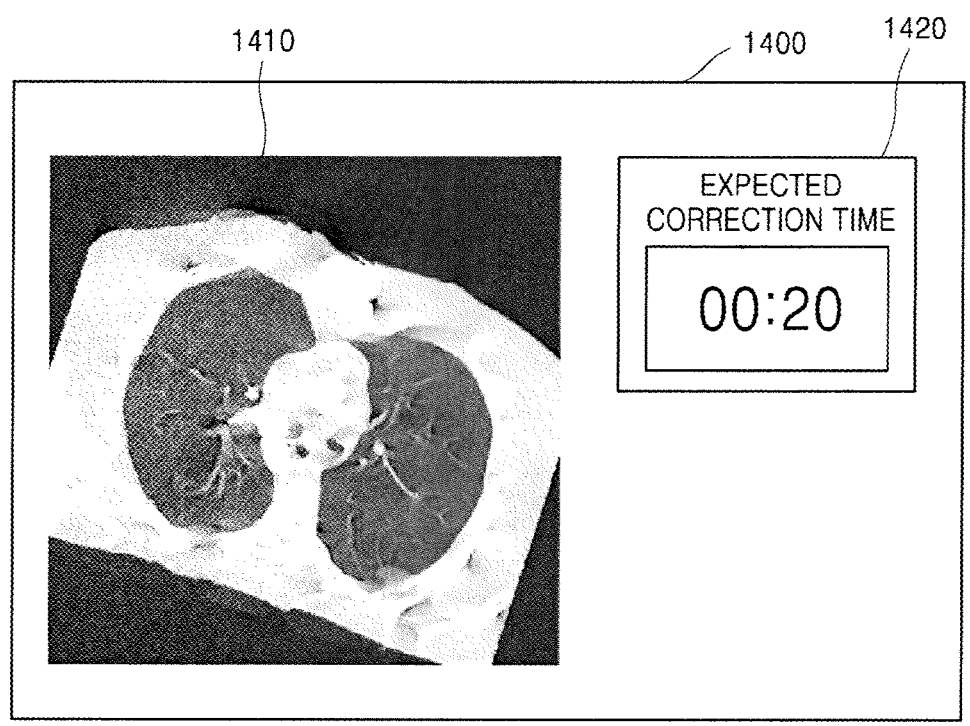
FIG. 14 is a diagram which illustrates an example of a UI indicating an expected time needed for a CT apparatus to correct motion artifacts in a reconstruction image, according to an embodiment of the disclosure.

FIG. 14 illustrates an example of a UI indicating an expected time needed for a CT apparatus to correct motion artifacts in a reconstruction image, according to an embodiment of the disclosure.

Referring to FIG. 14, the CT apparatus may display on a display 1400 a reconstruction image (a CT image) 1410 and a UI 1420 indicating an expected time needed to correct motion artifacts in the reconstruction image 1410. According to an embodiment of the disclosure, the display 1400 may display the reconstruction image 1410 in a first region and the UI 1420 indicating the expected time needed for correction in a second region.

According to an embodiment of the disclosure, the CT apparatus may receive a user input of selecting one from among regions having motion artifacts in the reconstruction image 1410, and the display 1400 may display the UI 1420 indicating the expected time needed to correct the region with motion artifacts selected according to the received user input.

According to the embodiment, by displaying the expected time needed for correction in advance, the CT apparatus may allow the user to quickly determine whether to perform correction or another CT imaging. Furthermore, when another CT imaging is to be performed, it is possible to reduce the unnecessary time required for correction and thus improve efficiency.

Figure 15:
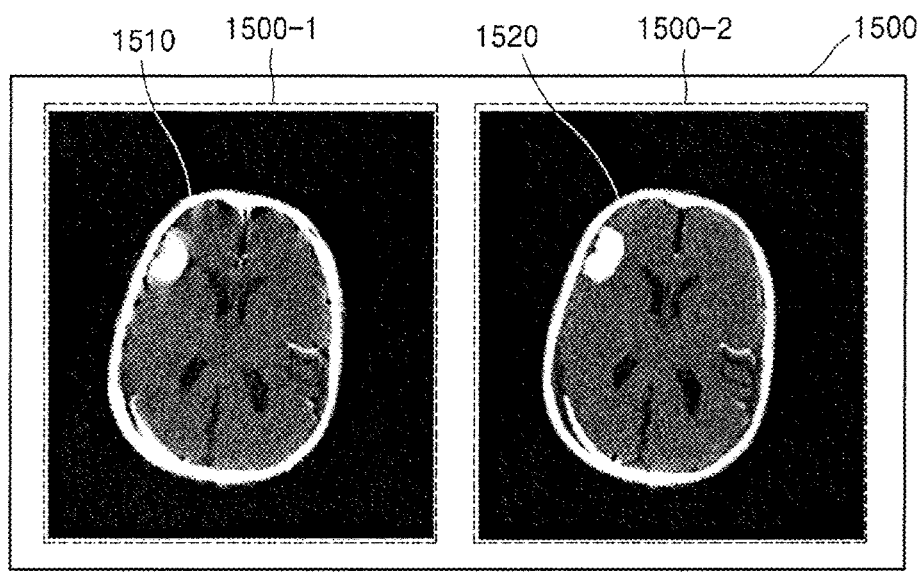
FIG. 15 is a diagram which illustrates an example in which a CT apparatus displays reconstruction images respectively obtained before and after undergoing correction, according to an embodiment of the disclosure.

FIG. 15 illustrates an example in which a CT apparatus displays CT images respectively obtained before and after undergoing correction, according to an embodiment of the disclosure.

Referring to FIG. 15, the CT apparatus may display on a display 1500 a first image 1510, i.e., a CT image on which correction has not been performed together with a second image 1520, i.e., a CT image obtained by performing correction. According to an embodiment of the disclosure, the display 1500 may display the first image 1510 in which motion artifacts have not been corrected in a first region 1500-1 and the second image 1520 in which motion artifacts have been corrected in a second region 1500-2. As seen on the first and second images 1510 and 1520, the first image 1510 may have many motion artifacts that appear more blurred and less sharp than those in the second image 1520.

According to the embodiment, the CT apparatus may display in parallel the first image 1510 that is a CT image reconstructed from an X-ray projection image and the second image 1520 that is a CT image obtained by performing correction for removing motion artifacts in the first image 1510, thereby allowing the user to quickly identify which part of the motion artifacts has been corrected and the degree of the correction and accordingly, improving user convenience.

The embodiments of the disclosure described above with reference to FIGS. 1 through 15 may be embodied in form of a computer-readable recording medium for storing computer executable command languages and data. The command languages may be stored in form of program codes and, when executed by a processor, may perform a certain operation by generating a certain program module. Also, when executed by a processor, the command languages may perform certain operations of the disclosed embodiments.

While embodiments of the disclosure have been particularly shown and described with reference to the accompanying drawings, it will be understood by those of ordinary skill in the art that various changes in form and details may be made therein without departing from the spirit and scope of the disclosure as defined by the appended claims. The disclosed embodiments should be considered in descriptive sense only and not for purposes of limitation.

What is claimed is:

1. A method of correcting a computed tomography image, the method comprising:
   obtaining a reconstruction image of an object by reconstructing an X-ray projection image;
   measuring a parameter value related to motion artifacts that occur due to movement of the object in at least one of the X-ray projection image or the reconstruction image, the measuring the parameter value including measuring a relative change in positions of edges of the object, in a plurality of X-ray projection images acquired by emitting X-rays toward the object at different time points;
   calculating a correction probability value to correct the reconstruction image based on the measured parameter value; and
   determining whether to perform correction on the reconstruction image based on the calculated correction probability value.

2. The method of claim 1, further comprising receiving a user input setting a region to be corrected in the reconstruction image,
   wherein the calculating the correction probability value comprises calculating a correction probability value for the region to be corrected, which is set according to the received user input, based on a parameter value measured in the set region.

3. The method of claim 1, further comprising:
measuring a first position that is a position of an edge in a first X-ray projection image acquired at a first angular position; and
measuring a second position that is a position of the edge in a second X-ray projection image acquired at the first angular position after moving the object by a pitch with a preset interval in a first direction, and
wherein the calculating the correction probability value comprises calculating the correction probability based on a difference between the pitch and a difference between the first and second positions.

4. The method of claim 1, further comprising:
storing a correction result value with respect to the parameter value, which is received from a user; and
training a correlation between the received correction result value and the parameter value by using machine learning,
wherein the calculating the correction probability value comprises updating an equation used to calculate the correction probability value by receiving the trained correlation as feedback data.

5. The method of claim 1, further comprising displaying the calculated correction probability value.

6. The method of claim 5, wherein the displaying the correction probability value comprises displaying a color mapping image obtained by mapping a color corresponding to the calculated correction probability value onto the reconstruction image.

7. The method of claim 1, further comprising displaying a user interface (UI) indicating an expected time needed to perform the correction on the reconstruction image when it is determined that the correction is to be performed on the reconstruction image.

8. The method of claim 1, further comprising displaying a corrected image obtained by performing the correction with respect to the reconstruction image in a first region of a display and the reconstruction image on which the correction has not been performed in a second region of the display.

9. A computed tomography (CT) apparatus comprising:
an X-ray source configured to emit X-rays toward an object at a plurality of angular positions arranged around the object;
an X-ray detector configured to detect the X-rays that have passed through the object at positions corresponding to the plurality of angular positions;
a data acquisitor configured to acquire a plurality of X-ray projection images based on the X-rays detected by the X-ray detector;
an image generator configured to generate a reconstruction image by reconstructing the plurality of X-ray projection images; and
a processor configured
to measure a parameter value related to motion artifacts that occur due to movement of the object in at least one of the plurality of X-ray projection images or the reconstruction image, the measuring the parameter value including measuring a relative change in positions of edges of the object, in a plurality of X-ray projection images acquired by emitting X-rays toward the object at different time points,
to calculate a correction probability value to correct the reconstruction image based on the measured parameter value, and
to determine whether to perform correction on the reconstruction image based on the calculated correction probability value.

10. The CT apparatus of claim 9, further comprising a user inputter configured to receive a user input to set a region to be corrected in the reconstruction image,
wherein the processor is further configured to set the region to be corrected based on the received user input and to calculate a correction probability value for the region to be corrected based on a parameter value measured in the region to be corrected.

11. The CT apparatus of claim 9, wherein the processor is further configured to measure a first position that is a position of an edge in a first X-ray projection image acquired at a first angular position, measure a second position that is a position of the edge in a second X-ray projection image acquired at the first angular position after moving the object by a pitch with a preset interval in a first direction, and calculate the correction probability value based on a difference between the pitch and a difference between the first and second positions.

12. The CT apparatus of claim 9, wherein the processor comprises:
a memory storing the correction result value with respect to the parameter value, which is received from a user; and
a machine learning module configured to train a correlation between the received correction result value and the parameter value by using machine learning and update an equation used to calculate the correction probability value by receiving the trained correlation as feedback data.

13. The CT apparatus of claim 9, further comprising a display displaying the calculated correction probability value.

14. The CT apparatus of claim 13, wherein the display further displays a color mapping image obtained by mapping a color corresponding to the calculated correction probability value onto the reconstruction image.

15. The CT apparatus of claim 13, wherein the display further displays a corrected image obtained by performing the correction with respect to the reconstruction image in a first region of a display and the reconstruction image on which the correction has not been performed in a second region of the display.

16. A computer program product comprising a non-transitory computer-readable storage medium instructions executable by a computer to cause the computer to perform a method comprising:
obtaining a reconstruction image of an object by reconstructing an X-ray projection image;
measuring a parameter value related to motion artifacts that occur due to movement of the object in at least one of the X-ray projection image or the reconstruction image, the measuring the parameter value including measuring a relative change in positions of edges of the object, in a plurality of X-ray projection images acquired by emitting X-rays toward the object at different time points;
calculating a correction probability value to correct the reconstruction image based on the measured parameter value; and
determining whether to perform correction on the reconstruction image based on the calculated correction probability value.

17. The computer program product as claimed in claim 16, wherein the method performed by the computer executing the instructions further comprises:
- measuring a first position that is a position of an edge in a first X-ray projection image acquired at a first angular position; and
- measuring a second position that is a position of the edge in a second X-ray projection image acquired at the first angular position after moving the object by a pitch with a preset interval in a first direction,
- wherein the calculating the correction probability value comprises calculating the correction probability based on a difference between the pitch and a difference between the first and second positions.

* * * * *